(12) United States Patent
Kobayashi

(10) Patent No.: US 7,526,061 B2
(45) Date of Patent: Apr. 28, 2009

(54) COMPUTERIZED TOMOGRAPHY DEVICE USING X RAYS AND IMAGE PROCESSING METHOD

(75) Inventor: Masaki Kobayashi, Ome (JP)

(73) Assignee: Aloka Co., Ltd., Tokyo (JP)

( * ) Notice: Subject to any disclaimer, the term of this patent is extended or adjusted under 35 U.S.C. 154(b) by 261 days.

(21) Appl. No.: 11/517,093

(22) Filed: Sep. 7, 2006

(65) Prior Publication Data

US 2007/0053485 A1 Mar. 8, 2007

(30) Foreign Application Priority Data

Sep. 8, 2005 (JP) ............................. 2005-261003
Sep. 8, 2005 (JP) ............................. 2005-261004

(51) Int. Cl.
*A61B 6/03* (2006.01)
(52) U.S. Cl. ........................... 378/4; 378/901; 382/131; 382/133
(58) Field of Classification Search ...................... 378/4, 378/8, 19, 901; 382/128, 131, 133
See application file for complete search history.

(56) References Cited

U.S. PATENT DOCUMENTS 5,260,871 A * 11/1993 Goldberg .................... 382/128
2004/0228434 A1 * 11/2004 Tsujii ............................ 378/4
2004/0264628 A1 * 12/2004 Besson .......................... 378/5

FOREIGN PATENT DOCUMENTS

| JP | 2002-222410 | 8/2002 |
|---|---|---|
| JP | 2003-061949 | 3/2003 |
| JP | 2003-339694 | 12/2003 |
| JP | 2004-057275 | 2/2004 |
| JP | 2004-113484 | 4/2004 |
| JP | 2005-192656 | 7/2005 |
| JP | 2005-192657 | 7/2005 |

OTHER PUBLICATIONS

Minotti et al., "Positron Emission Tomography/Computed Tomography Fusion Imaging in Brown Adipose Tissue", Clinical Nuclear Medicine, Jan. 2004, vol. 29(1), pp. 5-11.*
Anthony J. Ninnotti et al., "Position Emission Tomography/Computed Tomography Imaging in Brown Adipose Tissue", Jan. 2004, U.S. National Library of Medicine, U.S.

* cited by examiner

*Primary Examiner*—Chih-Cheng G Kao
(74) *Attorney, Agent, or Firm*—William L. Androlia; H. Henry Koda

(57) ABSTRACT

A computerized tomography device using an X-ray reconstructs a CT image of a sample and processes the CT image. Brown adipose candidate pixels are extracted based on a CT number of each pixel reconstructing the CT image. An erroneous pixel removal process is applied to the candidate pixels. In the erroneous pixel removal process, a boundary pixel removal process, a contraction and expansion process, or the like are applied. With this process, only the brown adipose pixels are extracted. An amount of brown adipose is determined from the brown adipose pixels and an evaluation value such as a brown adipose percentage is calculated based on the amount of brown adipose and amounts of other tissues.

30 Claims, 16 Drawing Sheets

| R1 | R2 | R3 |
|----|----|----|
| R4 | Q  | R5 |
| R6 | R7 | R8 |

COMPUTERIZED TOMOGRAPHY DEVICE USING X RAYS AND IMAGE PROCESSING METHOD

BACKGROUND OF THE INVENTION

1. Field of the Invention

The present invention relates to a computerized tomography (CT) device using X rays and an image processing method, and, in particular, to a CT image processing technique for extracting a predetermined tissue.

2. Description of the Related Art

It is known that adipose tissues (fat cells) present in a body of a living body (humans and other animals) can be divided into two types, white adipose tissue and brown adipose tissue. White adipose tissue stores energy as a triglyceride and provides energy to the body as prompted. Brown adipose tissue provides a highly advanced thermogenesis or calorigenic action. An increase and an activation of the brown adipose cause reduction in the white adipose which causes adiposis or obesity. Because of this, brown adipose has recently attracted much attention in the medical field. White adipose is present in a large amount in the abdomen, the buttocks, the thighs, the back, the upper arms, regions around internal organs, etc. According to recent research, the brown adipose, on the other hand, is present in a small amount only in specific regions such as, for example, the area behind the neck and that part of the back near the scapula.

Japanese Patent Laid-Open Publication No. 2003-339694 discloses a device which distinguishes between subcutaneous fat and visceral fat based on a CT (computerized tomography) image created through an X-ray measurement. There is, however, no device or method for automatically identifying and extracting images of brown adipose.

In order to quantify the brown adipose on a CT image, a method can be considered in which the brown adipose is manually determined or identified by a user viewing the CT image. With such manual determination, however, the objectivity or reliability of the quantification result of the brown adipose is reduced. In particular, when the brown adipose cannot be clearly distinguished from other tissues on the CT image, the precision of identification is significantly lowered. Moreover, with the manual operation, a large work is required and the process cannot be quickly performed. In particular, when a volume of the brown adipose is to be determined based on a plurality of CT images, these problems become more significant.

SUMMARY OF THE INVENTION

The present invention advantageously enables automatic identification of brown adipose based on a CT image.

The present invention also advantageously enables obtaining information for evaluating the brown adipose while precisely identifying the brown adipose based on the CT image.

According to one aspect of the present invention, there is provided an X-ray computerized tomography device comprising an X-ray generator which irradiates a sample with an X-ray beam, an X-ray detector which detects an X-ray beam transmitting through the sample, a rotation mechanism which rotates the X-ray beam relatively with respect to the sample, an image formation unit which reconstructs a CT image based on an output signal of the X-ray detector, and an image processor which applies an image process to the CT image to distinguish brown adipose in the sample from other tissues.

In the above-described structure, when an X-ray beam is irradiated by the X-ray generator, the X-ray beam transmits through the sample and is detected by the X-ray detector. The X-ray beam is irradiated in such a manner as to rotationally scan the sample; to accomplish this relative rotation, either the X-ray beam or the sample may be rotated. In order to reconstruct a plurality of CT images, the sample is moved with respect to the X-ray beam and scanned. In this case also, either the sample or the X-ray beam may be moved. The image formation unit reconstructs a CT image based on an output signal of the X-ray detector. The image processor applies an image process to the CT image for extracting the brown adipose. A quantification calculation may be applied to the extracted brown adipose or an image of the extracted brown adipose may be displayed. The sample is an animal or a human.

The X-ray CT device according to the present invention has a brown adipose measuring function which is not provided in the X-ray CT devices of the related art. By executing this function, it is possible to automatically extract the brown adipose through analysis of the CT image, and, thus, various problems caused in the case of the manual extraction can be resolved. In other words, with the above-described structure, it is possible to extract the brown adipose with a high precision and the extraction process is automatically executed under an objective standard. Therefore, the device has a superior reproducibility and the reliability of the measurement result can be improved because of this characteristic. It is also possible to employ a configuration in which the brown adipose is automatically extracted within a two-dimensional region of interest or a three-dimensional region of interest designated by the user.

According to another aspect of the present invention, it is preferable that, in the X-ray computerized tomography device, an evaluation value related to a percentage of the brown adipose is calculated based on the amount of brown adipose. Even when an accurate evaluation cannot be provided for a sample based solely on the amount of the brown adipose, by determining an evaluation value based on the amount of brown adipose and in consideration of other information (or reflecting other information in the amount of brown adipose), it is possible to objectively or comprehensively evaluate the sample. The evaluation value may be, for example, a brown adipose percentage, a ratio of brown adipose in total fat, an anti-adiposis parameter (an index indicating a relative degree of unlikelihood of becoming obese), etc.

According to another aspect of the present invention, there is provided an image processing method in which a CT image obtained through an X-ray computerized tomography measurement with respect to a sample is processed, the method comprising a first extraction step in which candidate pixels which may belong to a brown adipose are extracted from a group of pixels reconstructing the CT images based on a CT number of each pixel, and a second extraction step in which an erroneous pixel removal process is applied to the candidate pixels to extract brown adipose pixels.

According to the above-described method, it is possible to identify candidate pixels based on the CT value on the CT image and then remove erroneous pixels included in the candidate pixels, to identify the brown adipose pixels. For example, in a region such as a boundary between the white adipose and muscle and a thin muscle layer, a pixel having a CT number similar to the CT number of the brown adipose pixel may be observed. By applying a process to remove these erroneous pixels, the identification precision of the brown adipose and reliability of quantification calculation result can be improved.

According to another aspect of the present invention, it is preferable that, in the image processing method, an evaluation value useful for health management and disease diagnosis is calculated based on the extracted brown adipose pixels. With the evaluation value, it is possible to objectively or comprehensively evaluate a sample.

BRIEF DESCRIPTION OF THE DRAWINGS

A preferred embodiment of the present invention will be described in detail based on the following figures, wherein.

DESCRIPTION OF PREFERRED EMBODIMENT

Figure 1:
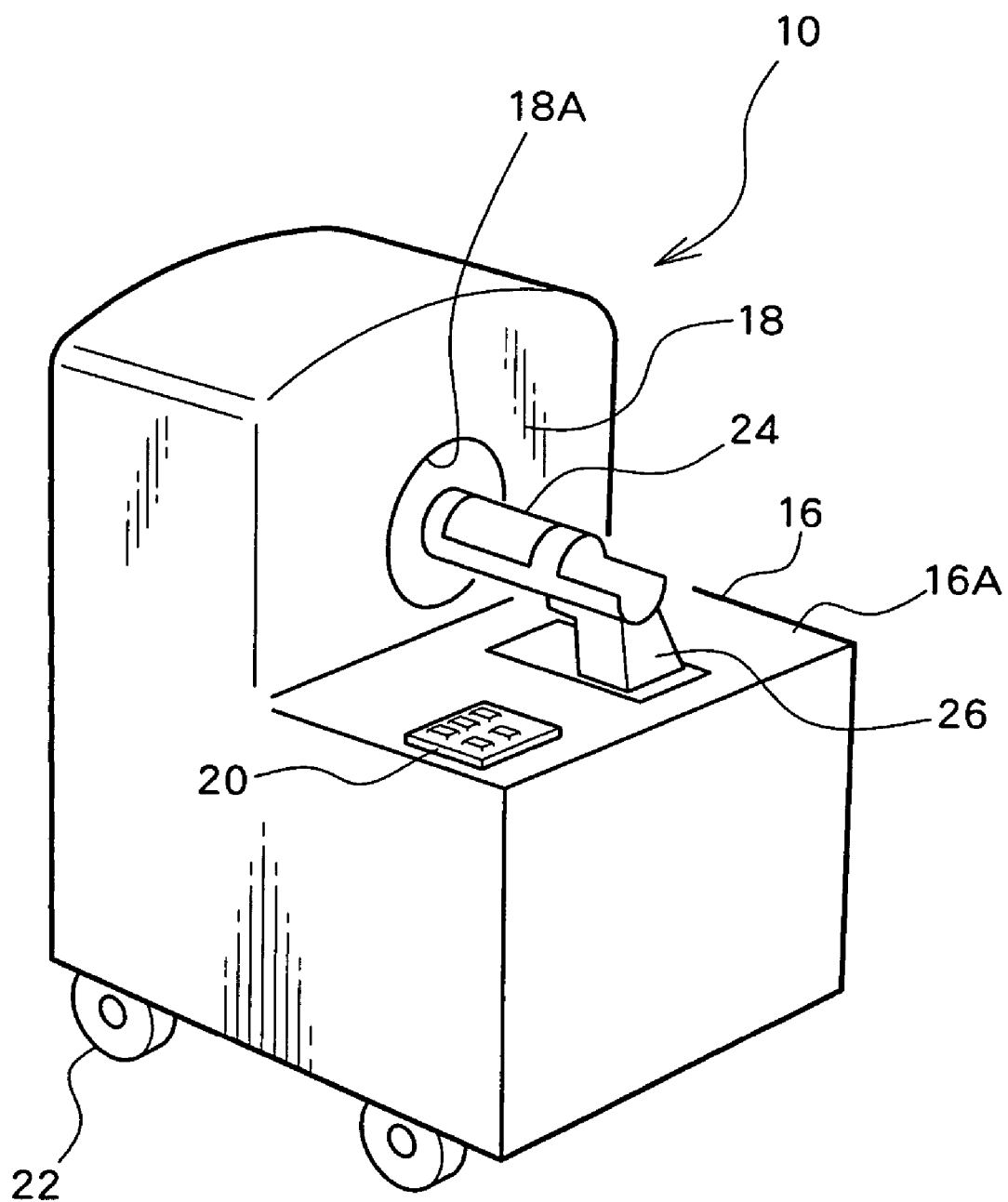
FIG. 1 is a perspective view exemplifying a measurement unit in an X-ray CT device according to a preferred embodiment of the present invention.

A preferred embodiment of the present invention will now be described.

(1) Summary of X-ray CT Device in the Preferred Embodiment

An X-ray computerized tomography (CT) device of the preferred embodiment of the present invention comprises an X-ray generator, an X-ray detector, a rotation mechanism, a scan mechanism, an image formation unit, an image processor, and a calculation unit, as will be described later in detail. The image formation unit comprises a first extraction unit (first extraction function) and a second extraction unit (second extraction function). The first extraction unit extracts candidate pixels from among a group of pixels reconstructing a CT image based on a CT number of each pixel. Each candidate pixel is a pixel which may depict brown adipose. The second extraction unit applies an erroneous pixel removal process to the candidate pixels, to extract brown adipose pixels. The extracted brown adipose pixels form a brown adipose image. When there are no erroneous pixels among the candidate pixels, or when there are substantially no erroneous pixels among the candidate pixels, it is possible to provide only the first extraction unit and to assume that the candidate pixels are brown adipose pixels. However, as various erroneous pixels are normally present among the candidate pixels, various applicable erroneous pixel removal processes will be described below. The calculation unit calculates the amount of brown adipose based on the identified brown adipose and calculates an evaluation value related to a presence ratio of the brown adipose in the sample based on the amount of brown adipose. The amount of brown adipose (and amount of other tissues to be described below) can be expressed as a number of pixels, an area, a volume, or a weight.

The image formation unit, image processor, and calculation unit can be provided by dedicated hardware or as a function of software. The sample to be measured is a human or other animal. Animals include, for example, small animals such as rats, mice, and hamsters. It is also possible to measure other animals such as, for example, dogs, cats, and pigs.

Preferably, the first extraction unit determines, for each pixel forming a group of pixels, whether or not a CT number of the pixel is within a predetermined range and identifies a pixel having the CT number within the predetermined range as a candidate pixel. More specifically, because each type of tissue has a CT number approximately within a constant range (the constant range, however, depending on the structure and operation condition of the device), the tissue can be identified based on the CT number. An upper limit of the predetermined range is set at a CT number between a standard CT number of muscle and a standard CT number of brown adipose and a lower limit of the predetermined range is set at a CT number between a standard CT number of white adipose and the standard CT number of brown adipose. In general, the candidate pixels in the predetermined range include pixels that are not brown adipose pixels (erroneous pixels), and, thus, the second extraction unit is provided in order to remove the erroneous pixels.

Preferably, the erroneous pixel removal process at the second extraction unit includes a first process. In the first process, when a pixel having a CT number which is higher than a first threshold value and a pixel having a CT number which is lower than a second threshold value are present around a candidate pixel of interest, the candidate pixel of interest is determined to be an erroneous pixel and removed. According to experiments and research conducted by the present inventors, a pixel having a CT number which appears to be similar to the CT number of brown adipose may occur, for example, between muscle and white adipose. Because the CT number of muscle is higher than the CT number of the brown adipose and the CT number of the white adipose is lower than the CT number of the brown adipose, an intermediate CT number may be calculated in the boundary between the muscle and the white adipose. By applying the first process, the erroneous pixels can be removed taking advantage of a property of the boundary structure.

Preferably, the erroneous pixel removal process at the second extraction unit includes a second process. In the second process, a non-brown adipose pixel satisfying a predetermined condition is identified in the CT image, and a candidate pixel is determined to be an erroneous pixel and removed when the candidate pixel is adjacent to the non-brown adipose pixel. Preferably, the predetermined condition is a condition to determine a pixel having a CT number which is higher than a third threshold value as the non-brown adipose pixel or a condition to determine a pixel having a CT number which is lower than a fourth threshold value as the non-brown adipose pixel. With such a configuration, a tissue pixel other than brown adipose pixel (that is, non-brown adipose pixel) is set as a reference, and a candidate pixel is identified as an erroneous pixel when the candidate pixel is adjacent to the tissue. A pixel having a CT number similar to the CT number of the brown adipose may occur, for example, at a boundary of tissues and in a thin muscle layer. With the above-described structure, such an erroneous pixel can be removed.

Preferably, the erroneous pixel removal process at the second extraction unit includes a third process. In the third process, after a contraction process is applied to the candidate pixels, an expansion process is applied to the contracted candidate pixels. With the contraction process, a thin erroneous layer can be deleted, but a region around the true brown adipose region is also cut. With the application of the expansion process, however, only the true brown adipose region can be restored almost to the original region. Thus, with the third process, the precision of the quantification calculation can be improved. When the contraction process is applied N times (where $N \geq 1$), the expansion process is also applied N times. In either case, the contraction and expansion process is effective when the erroneous tissue region is thinner or smaller than the true brown adipose region. With the contraction and expansion process, erroneous pixel which is present in an isolated manner can also be removed.

Preferably, a voltage switching unit which switches a drive voltage of the X-ray generator is provided. In a normal measurement mode, a high voltage is selected as the drive voltage of the X-ray generator, while, on the other hand, in a brown adipose measurement mode, a low voltage is selected as the drive voltage of the X-ray generator. Preferably, a rotational speed switching unit is provided which switches a rotational speed of the X-ray beam. In the normal measurement mode, a high speed is selected as the rotational speed of the X-ray beam. In the brown adipose measurement mode, on the other hand, a low speed is selected as the rotational speed of the X-ray beam.

The X-ray CT device according to the present embodiment has a function to calculate an evaluation value based on an amount of brown adipose determined through a quantitative calculation of the brown adipose. More specifically, the image processor identifies a plurality of tissue areas which include brown adipose in a sample based on the CT image, and the calculation unit calculates amounts of a plurality of tissues including the amount of brown adipose based on the image processing result by the image processor and calculates an evaluation value based on the amounts of the plurality of tissues. With this structure, an evaluation value can be obtained in which the amounts of tissues other than the brown adipose are taken into consideration in addition to the amount of brown adipose. Thus, it is possible to comprehensively and objectively evaluate the sample. With this structure, it is possible to objectively compare, for example, measurement results between samples having different sizes (physical constitution) and to comprehensively evaluate a degree of obesity or tendency to not become obese. In addition, it is possible to evaluate constitutional predisposition from the viewpoint of percentage of brown adipose.

Preferably, the evaluation value is determined by calculating the amount of brown adipose and dividing this value by the sum of the amounts of the plurality of tissues. Preferably, the evaluation value is determined through a calculation of the amount of brown adipose divided by the weight of the sample. Preferably, the amounts of the plurality of tissues include the amount of white adipose in addition to the amount of brown adipose and the evaluation value is determined through a calculation of the amount of the brown adipose divided by a sum of the amount of brown adipose and the amount of white adipose. Preferably, the amounts of the plurality of tissues include the amount of muscle and the amount of the white adipose in addition to the amount of the brown adipose and the evaluation value is determined through a calculation of the amount of the brown adipose multiplied by the amount of the muscle divided by the amount of white adipose. Preferably, the amounts of the plurality of tissues include the amount of muscle and the amount of visceral fat in addition to the amount of brown adipose and the evaluation value is determined through a calculation of the amount of the brown adipose multiplied by the amount of the muscle divided by the amount of the visceral fat.

(2) Details of the X-ray CT Device in the Preferred Embodiment

Figure 2:
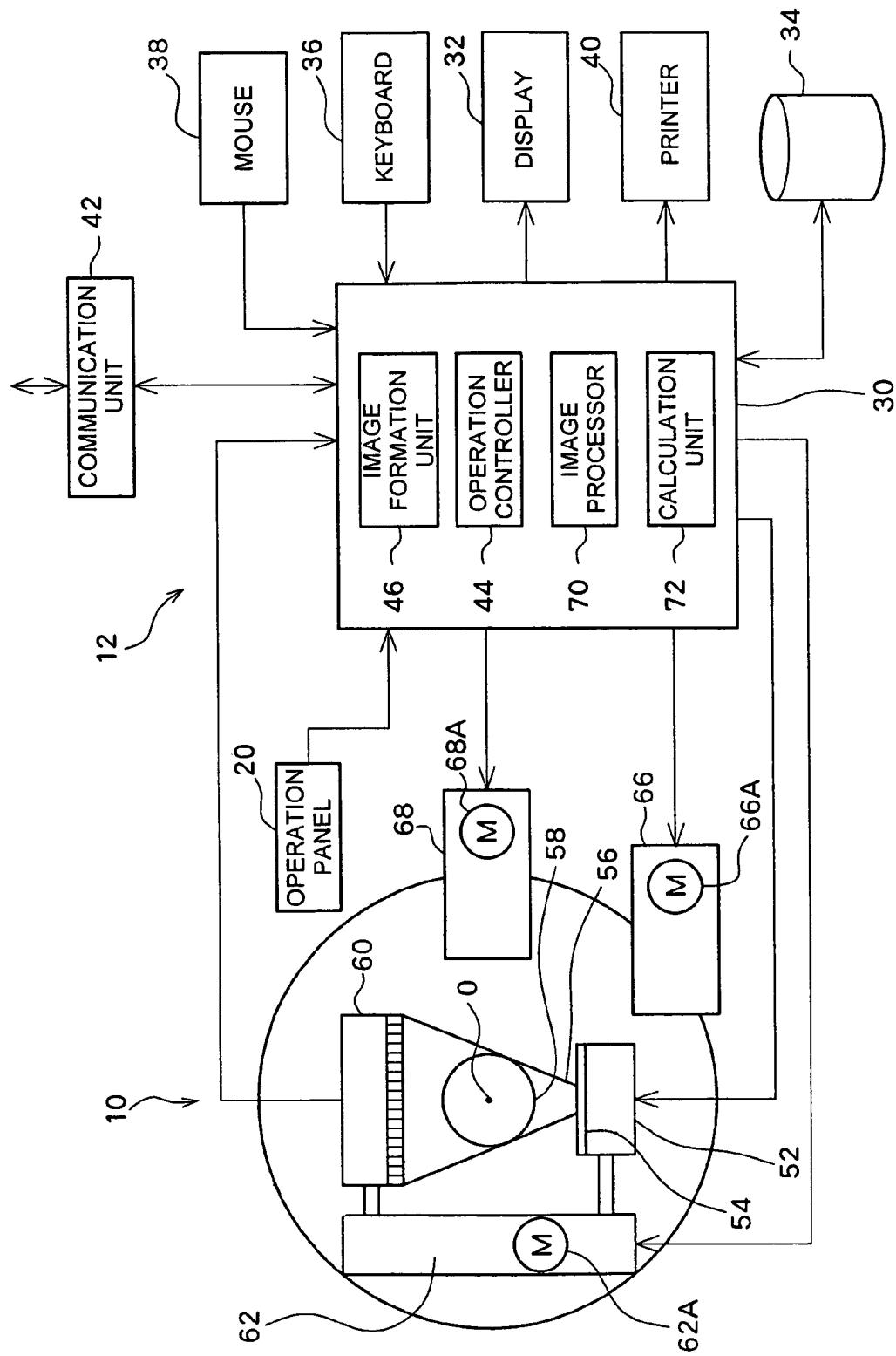
FIG. 2 is a block diagram showing a preferred embodiment of an X-ray CT device according to the present invention.

FIG. 1 shows an example of a measurement unit 10 in the X-ray CT device. The X-ray CT device of the preferred embodiment is a device particularly for CT-measuring the rats family including mice, rats, guinea pigs, and hamsters used in animal experiments. It is also possible to employ a configuration in which a tissue separated from the small animal is measured. As shown in FIG. 2, the X-ray CT device comprises the measurement unit 10 and a calculation controller.

In FIG. 1, the measurement unit 10 comprises a body 16 having a gantry 18. An opening is formed on an upper surface 16A of the body 16 and an arm 26 protrudes in an upward direction through the opening. The arm 26 is a part of a sliding mechanism which will be described later, and is connected to a container 24, to slide and move the container 24 along a direction of the center axis of rotation (moving scan).

A measurement unit (X-ray generator and X-ray detector) to be described later is stored within the gantry 18 and rotationally moves around the center axis of rotation. A cavity portion 18A is formed along the direction of center axis of rotation in a center portion of the gantry 18. The cavity portion 18A is formed as a non-penetrating type, but the cavity portion 18A may be of a penetrating type.

In the present embodiment, the container 24 is a capsule which stores a sample (a small animal or a tissue isolated from the small animal) and has an approximate tube shape. The container 24 is placed with the center axis of the container matching the center axis of rotation. More specifically, a base end of the container 24 is detachably attached to an upper end of the arm 26. In this case, as the detachable mechanism, for example, various engaging mechanisms and screwing mechanism may be employed. As described above, the container 24 has a hollow tube shape, and, in the present embodiment, one or a plurality of small animals is placed inside the tube. With such a structure, it is possible to prevent, for example, the hair of the small animal from directly contacting the gantry 18. In addition, it is also possible to prevent a problem of leakage, to the outside, of excrement or shed hair of the small animals. In addition, because it is possible to constrain the small animal within the container 24 by a fixture, it is possible to prevent problems such as image blurring when the CT image is to be reconstructed. It is preferable to prepare a plurality of types of containers having different sizes and shapes, and select a container from among the prepared containers.

After the container 24 is attached to the arm 26, the arm 26 is driven in a forward direction along the direction of the center axis of rotation and the container 24 is inserted into the cavity portion 18A of the gantry 18. In this process, the container 24 is positioned so that the X-ray beam is set at a measurement position of the sample. The measurement position is continuously or stepwise changed. As a result, a plurality of CT images (cross sectional images) are reconstructed which are spatially aligned with a predetermined pitch.

An operation panel 20 is provided on the upper surface 16A of the body 16 and comprises a plurality of switches and a display device. A user can operate the device in the measurement site using the operation panel 20. A plurality of casters 22 are provided below the body 16.

In the present embodiment, the rotational speed of the measurement unit in the gantry 18 can be stepwise or continuously changed. In addition, the drive voltage of the x-ray generator within the gantry 18 can be stepwise or continuously changed. As will be described later, in a normal measurement mode, a high rotational speed (or a normal rotational speed) and a high voltage (or a normal voltage) are selected. In a brown adipose measurement mode, on the other hand, a low rotational speed is selected and a low voltage is selected. The calculation controller to be described later has a switching function for the rotational speed and a switching function for the voltage.

FIG. 2 is a block diagram showing a structure of the X-ray CT device according to the present embodiment. In the measurement unit 10, an X-ray generator 52 is provided on one side and an X-ray detector 60 is provided on the other side with the center axis 0 of rotation therebetween. A collimator 54 is provided on an irradiation side of the X-ray generator 52. The X-ray generator 52 generates a spreading or fan-shaped (that is, fan beam shaped) X-ray beam 56, as shown in FIG. 2. The X-ray detector 60, on the other hand, is formed with a plurality of (for example, 100) X-ray sensors arranged in a line and a reception opening of X-ray is set according to an opening angle of the X-ray beam 56. The arrangement of the plurality of X-ray sensors may be a straight line or an arc shape. In the present embodiment, high-sensitivity X-ray sensors are used. In FIG. 2, a power supply connected to the X-ray generator 52, a signal processor circuit connected to the X-ray detector 60, etc. are not shown. A two dimensional X-ray sensor unit may be used as the X-ray detector 60.

In FIG. 2, a reference numeral 58 indicates an effective angle of view. The effective angle of view 58 is a circular region which can reconstruct a CT image when the X-ray beam 56 is rotationally scanned. The effective angle of view 58 is determined based on a positional relationship among the center axis of rotation, the X-ray generator 52, and the X-ray detector 60. In the present embodiment, a displacement mechanism 62 is provided, and, thus, the positional relationship can be changed to mechanically change the magnification of the CT image.

More specifically, the X-ray generator 52 and the X-ray detector 60 are connected to the displacement mechanism 62 and the displacement mechanism 62 displaces the X-ray generator 52 and the X-ray detector 60 (that is, the measurement unit) along the direction of the beam axis of an X-ray beam while maintaining the distance between the X-ray generator 52 and the X-ray detector 60. In this process, the center axis 0 of rotation is not changed. That is, the magnification can be changed by moving not the container, but the measurement unit. The displacement mechanism 62 has a motor 62A for generating a force for displacement.

A gantry rotation mechanism 66 is a mechanism which rotates a rotation base to rotationally drive all structures mounted on the rotation base including the displacement mechanism 62. Because the measurement unit is attached to the displacement mechanism 62, the measurement unit positioned at a desired position by the displacement mechanism 62 is rotationally driven while the position is maintained. The gantry rotation mechanism 66 has a motor 66A for generating the drive force.

A slide mechanism 68 is a movement mechanism for sliding and moving the arm 26 shown in FIG. 1 and is driven by a motor 68A. The operation panel 20 is provided at the upper surface of the body as described above. It is also possible to employ a configuration in which the operation panel 20 is connected to a local controller (not shown) provided on the side of the measurement unit 10 and the local controller and the calculation controller 12 communicate with each other.

For various mechanisms 62, 66, and 68 shown in FIG. 2, it is preferable to provide sensors for detecting the position or the positional change by these mechanisms. Preferably, the calculation controller 12 applies a feedback control based on output signals of the sensors. The change of magnification by the displacement mechanism 62 may be performed based on an input of a user or the magnification may be automatically set, for example, by automatically detecting the sample size or the container size and using the detected data. Alternatively, when a type of the container or the like is registered in advance, it is possible to set the magnification using the registered information. In the example configuration of FIG. 2, the sliding mechanism 68 has the motor 68A as the driving source, but the present invention is not limited to such a configuration and the sliding force may be manually generated.

The calculation controller 12 will next be described. A display 32, a storage device 34, a keyboard 36, a mouse 38, a printer 40, etc. are connected to a processor 30. In addition, a communication unit 42 is connected to the processor 30 for communicating with an external device via a network.

The processor 30 comprises a CPU and various programs. FIG. 2 shows primary functions, and the processor 30 has an operation controller 44, an image forming section 46, an image processor 70, a calculating section 72, etc. A scout image forming section or the like may be provided as necessary.

The operation controller 44 controls an overall operation of the measurement unit 10. The operation controller 44 has a function to switch the rotational speed, a function to switch the drive voltage of the X-ray generator 52, etc. Alternatively, it is also possible to employ a configuration in which the rotational speed and the drive voltage are designated by a user. In addition, it is also possible to employ a configuration in which the rotational speed and the drive voltage are automatically set according to a selected measurement mode when the user selects a measurement mode.

The X-ray CT device according to the present embodiment has a normal measurement mode and a brown adipose measurement mode. In the normal measurement mode, a high rotational speed is selected and a high voltage is selected. In the brown adipose measurement mode, on the other hand, a low rotational speed is selected and a low voltage is selected. According to the experiments and research by the present inventors, the brown adipose can be well distinguished on the CT image using the highly sensitive X-ray sensors and changing the operational conditions as described above.

When a small animal such as a mouse is the measurement target, a rotational speed of, for example, 10 rotations per minute is selected and a drive voltage of, for example, 70 kV is selected in the normal measurement mode. In the brown adipose measurement mode, on the other hand, a rotational speed of, for example, 1 rotation per minute is selected. In this case, the drive voltage can be set in a range of 20 kV-100 kV. Preferably, the drive voltage is set within a range of 30 kV-70 kV, and, more preferably, the drive voltage is set within a range of 30 kV-50 kV. The device used in the experiments by the present inventors was a commercially available Aloka Co., Ltd. X-ray CT device (Product name: LaTheta (registered trademark); model number: LCT-100). The numerical conditions may vary depending on various conditions such as, for example, the type of the sample and the structure of the X-ray CT device.

The image forming section 46 executes a calculation to reconstruct a CT image based on a set of data obtained by a rotational scan of the X-ray beam. Various known methods can be used for reconstruction calculation of the CT image.

The image processor 70 has a function to identify tissues (such as bone, muscle, white adipose, and brown adipose) based on the CT number of each pixel on the CT image. In particular, the image processor 70 has a novel function to apply a first extraction process and a second extraction process to a CT image to extract only the group of the brown adipose (brown adipose image). The extracted brown adipose data is converted to an image or supplied for quantitative calculation. The extraction method of the brown adipose will be described later.

The calculation section 72 executes a calculation for quantitatively evaluating the tissues based on the image processing result. In particular, the calculation section 72 has a function to calculate an amount of the brown adipose (for example, area, volume, weight, etc.) regarding the brown adipose, and, furthermore, has a function to calculate a predetermined evaluation value based on the amount of the brown adipose. The calculation method of the evaluation value will be described later in detail.

A CT image, a measurement result, etc. are displayed on the display 32. It is also possible to display the image of the brown adipose overlapping a background image of the scout image. In this case, it is also possible to employ a configuration in which the background image is displayed as a black-and-white image and the brown adipose image is displayed as a colored image. In this case, the overlapped image can alternatively be formed as a three-dimensional image.

Figure 3:
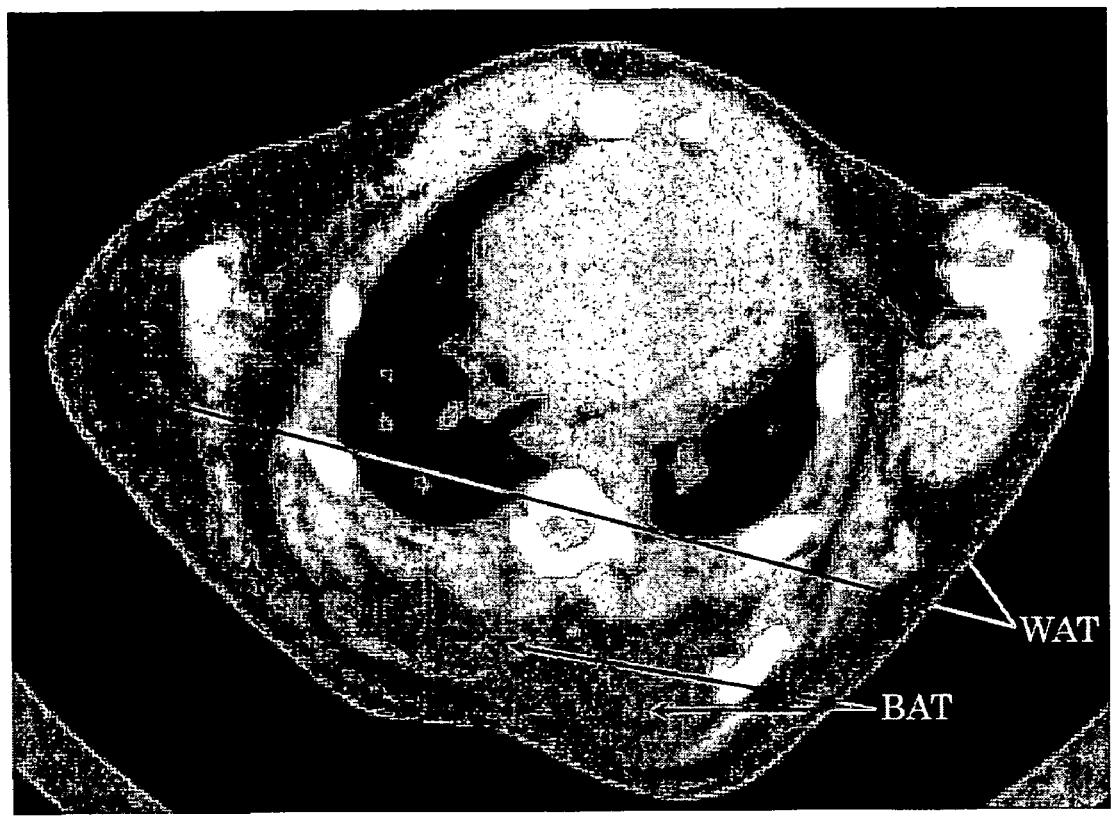
FIG. 3 is a diagram showing an example CT image.

FIG. 3 shows an example a CT image reconstructed by the X-ray CT device according to the present embodiment. The CT image is a cross sectional image of a mouse. WAT indicates the white adipose and BAT indicates the brown adipose. The brown adipose can be relatively clearly shown on the CT image under the optimum operational condition as described above. Under the above-described operational condition, the average (standard) CT number of the tissues and the identification range of the tissues are as shown in the following Table 1.

TABLE 1

| TISSUE | AVERAGE CT NUMBER (HU) | CT NUMBER RANGE (HU) |
|---|---|---|
| WHITE ADIPOSE | −250 | −500~−170 |
| BROWN ADIPOSE | −100 | −170~−20 |
| MUSCLE | 100 | −20~350 |
| BONE | 1000 OR GREATER | 350 OR GREATER |

As described, the CT number of the brown adipose is higher than the CT number of the white adipose and is lower than the CT number of the muscle. When, however, the operational condition of the device is not optimized, it is very difficult to distinguish between the brown adipose and the white adipose. More specifically, the amounts of the X-ray absorption of the white adipose and the brown adipose would be almost the same value. Therefore, it is preferable to find an optimum condition for measuring the brown adipose by suitably changing the operational condition of the device to take advantage of the characteristics of the X-ray (in particular, it is preferable to find a condition in which the difference in CT number between the white adipose and the brown adipose can be increased). Under the state in which the operational condition is optimized, as can be seen from the table shown above, it is possible to identify a tissue to which a pixel belongs, based on the CT number of the pixel. However, as will be described later, a pixel having an intermediate CT number (erroneous pixel) occurs, for example, in a boundary between the white adipose and the muscle. In order to precisely extract the brown adipose, it is desirable to remove such an erroneous pixel.

(3) Extraction of Brown Adipose

A method of extracting the brown adipose from a CT image will now be described referring to FIGS. 4-16. First, FIG. 4 conceptually shows a flow of the extraction process.

Figure 5:
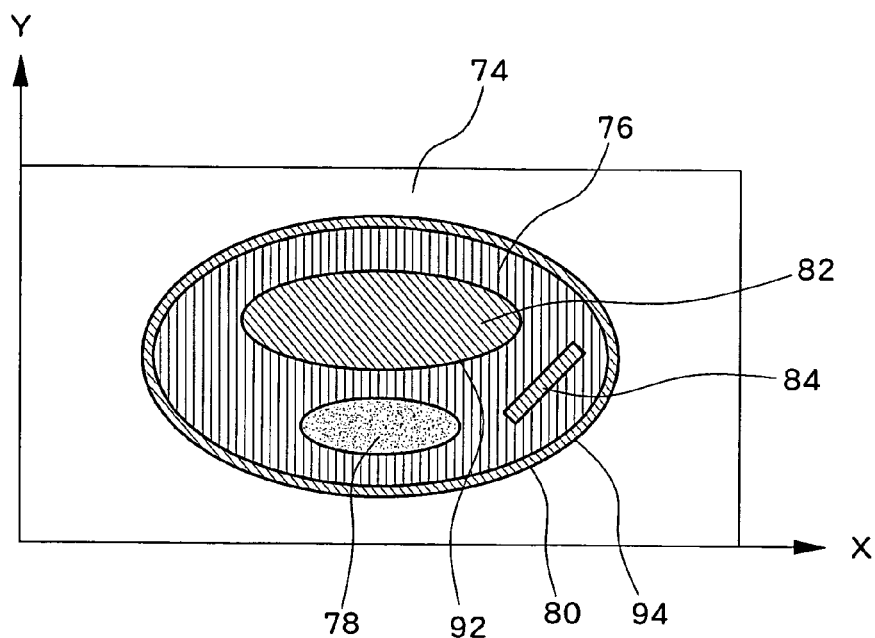
FIG. 5 is a diagram showing a CT image as a model.

A CT image shown in S101 is reconstructed by executing a reconstruction calculation (image formation calculation) indicated as S100 based on data output from the X-ray detector. FIG. 5, which will be described later, shows a CT image as a model.

Figure 4:
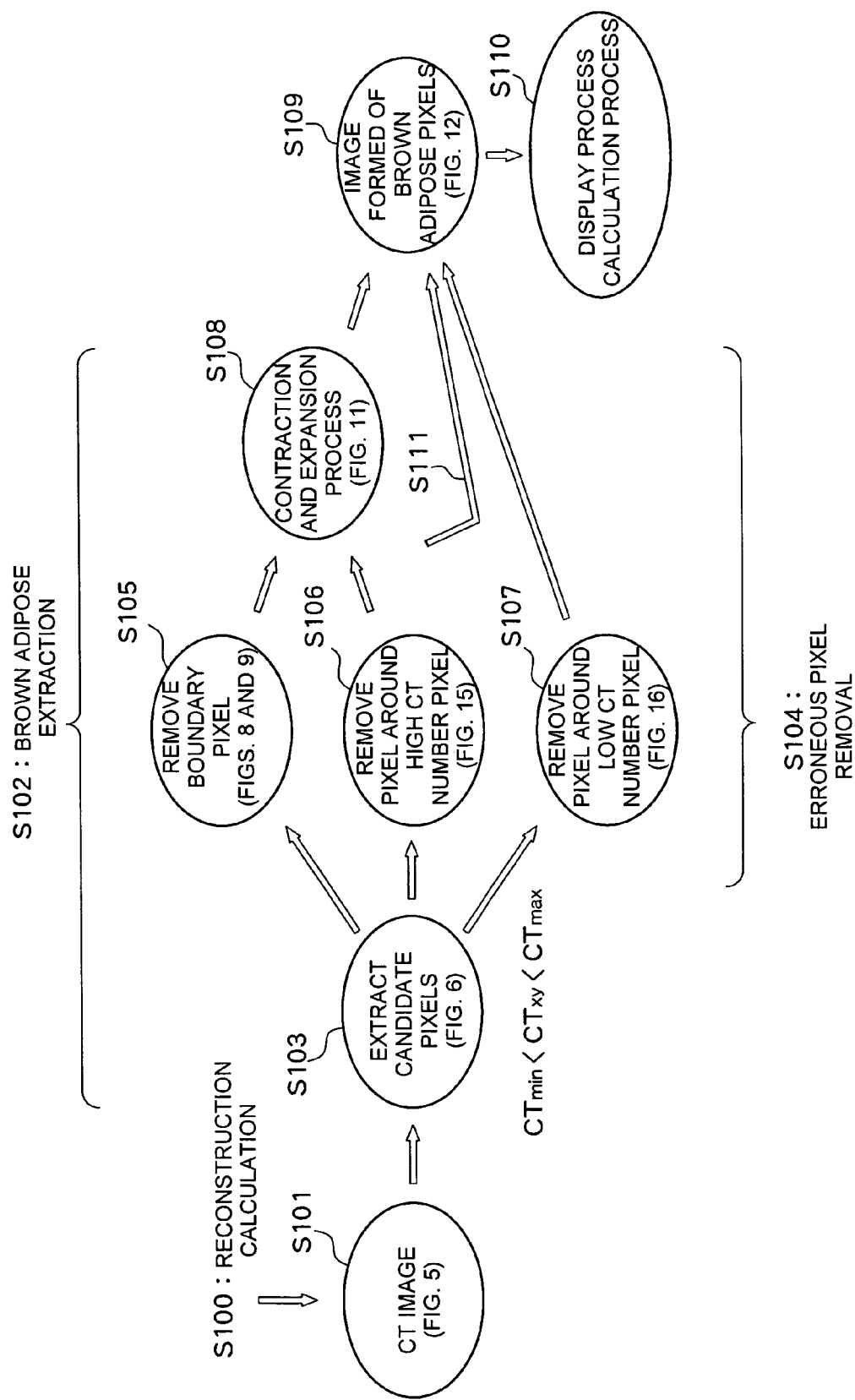
FIG. 4 is a flowchart for explaining a brown adipose extraction process.

S102 shows an overall extraction process of the brown adipose. The extraction process S102 mainly comprises a candidate pixel extraction process S103 which corresponds to a first extraction process and an erroneous pixel removal process S104 which is a second extraction process. In the candidate pixel extraction process S103, as will be described later referring to FIG. 6, candidate pixels which might correspond to the brown adipose are extracted from the CT image. In this process, a pixel having a CT number in a predetermined range among the pixels reconstructing the CT image is extracted as a candidate pixel. In the erroneous pixel removal process S104, a process is applied to identify erroneous pixels other than the brown adipose pixels in the candidate pixels and to remove the erroneous pixels (process to change these pixels into pixels other than the candidate pixels). Specific methods of the erroneous pixel removal process S104 include a number of methods. FIG. 4 shows a boundary pixel removal process S105 to be described later with reference to FIGS. 8 and 9, a contraction and expansion process S108 to be described later with reference to FIG. 11, a process S106 to remove pixels around high CT number pixels to be described later with reference to FIG. 15, and a process S107 to remove pixels surrounding low CT number pixels to be described later with reference to FIG. 16.

In the erroneous pixel removal process S104 shown in FIG. 4, S108 is executed after S105 is executed. Alternatively, it is also possible to employ a configuration in which S108 is executed after S106 is executed, or to employ a configuration in which only S107 is executed.

With any of these configurations, the brown adipose pixels can be extracted as a result of the candidate pixel extraction process S103 and the erroneous pixel removal process S104, as shown in S109. The brown adipose pixels form a brown adipose image, which will be described referring to FIG. 12. When the brown adipose image is obtained, a display process with respect to the brown adipose image is applied in S110 or a process for quantitatively calculating the brown adipose is executed. Either or both of the brown adipose image or a numerical value showing an amount of brown adipose is displayed on the display screen of the display. The X-ray CT device according to the present embodiment further has an evaluation value calculating function which will be described later referring to FIG. 17.

Specifics of the processes shown in FIG. 4 will now be described. FIG. 5 shows a CT image 74 shown as a model. An image process to be described below is executed for each CT image. In FIG. 5, an X-axis and a Y-axis are defined as the coordinate system of the CT image. A reference numeral 76 indicates white adipose. A reference numeral 80 indicates muscle including skin. Reference numerals 82 and 84 both indicate muscle. The muscle indicated by the reference numeral 84 is a thin muscle layer. A reference numeral 78 indicates brown adipose to be extracted. A reference numeral 92 indicates a boundary between the white adipose 76 and the muscle 82 and a reference numeral 94 indicates a boundary between the muscle 80 and the white adipose 76.

Figure 6:
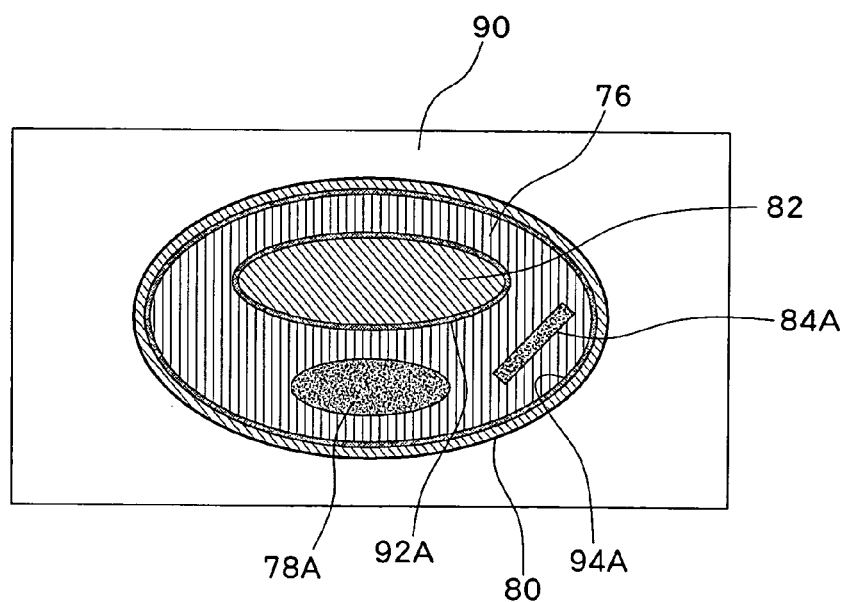
FIG. 6 is a diagram showing a result of an extraction process of candidate pixels.

FIG. 6 shows a result when the candidate pixel extraction process S103 shown in FIG. 4 is executed. In other words, a reference numeral 90 shows an image in which only the candidate pixels are identified. In the present embodiment, the CT number of each pixel reconstructing the CT image is checked and a pixel having the CT number within a predetermined range is identified as a candidate pixel according to the Table 1. More specifically, pixels satisfying the following condition are identified as candidate pixels:

$$CTmin < CTxy < CTmax \quad (1)$$

In equation (1), CTxy represents a CT number (HU) of a pixel at a coordinate of xy on the CT image. CTmin represents a lower limit of the predetermined range and has a value of, for example, −170. Similarly, CTmax represents an upper limit of the predetermined range and has a value of, for example, −20. In other words, it is possible to identify the brown adipose by referring to the CT number of each pixel in a CT image reconstructed under the optimum operational condition as described above. In reality, however, because the identified pixels may include pixels which belong to tissues other than the brown adipose, the erroneous pixel removal process is applied. More specifically, as shown in FIG. 6, the brown adipose is extracted, as shown by a reference numeral 78A, through a candidate pixel extraction process based on the CT number, but the pixels belonging to a tissue or site other than the brown adipose are also extracted as candidate pixels. In the example of FIG. 6, in the boundary 92A between the muscle 82 and the white adipose 76, pixels on the boundary 92A are extracted as the candidate pixels although these pixels are not brown adipose, because these pixels have CT numbers similar to the brown adipose. Similarly, an intermediate CT number appears in the boundary 94A between the white adipose 76 and the muscle 80 and the pixels on the boundary 94A are also extracted as candidate pixels. For a similar reason, the pixels on the thin muscle 84A are extracted as the candidate pixels. Thus, removal of these erroneous pixels is desired.

The site in which the brown adipose exists is generally limited to a region behind the neck and a specific site on the back. Thus, for quantitative measurement of the brown adipose, it is possible to measure the CT number only for specific sites of the sample. Alternatively, it is also possible to measure the CT number for the whole body.

The intermediate CT numbers occur because the white adipose has a lower CT number than the brown adipose as shown in Table 1, the muscle has a higher CT number than the brown adipose as shown in Table 1, and a CT number similar to the brown adipose is observed at the boundary between the white adipose and the muscle. The removal process of erroneous pixels will now be described in detail.

Figures 7, 8:
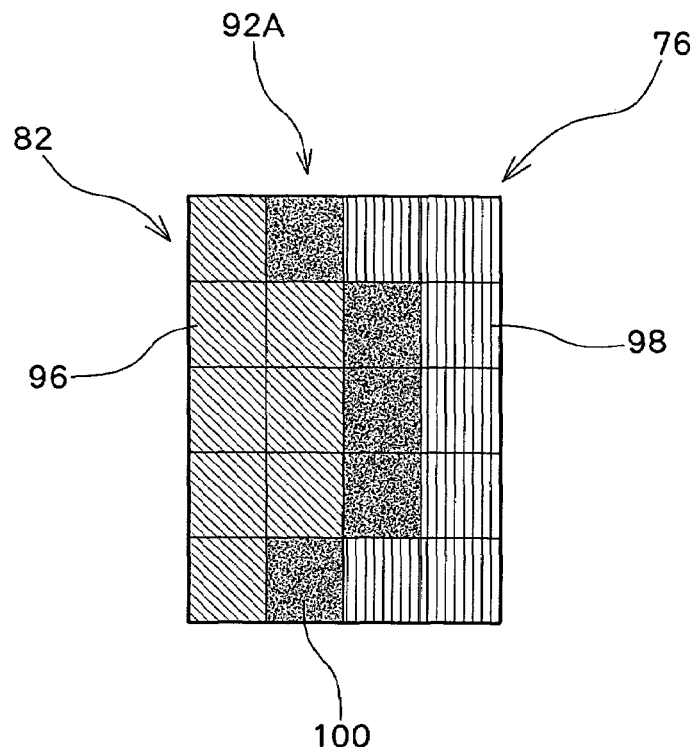
FIG. 7 is an enlarged view showing a line of candidate pixels on a boundary.
FIG. 8 is a diagram for explaining a filter used in a concurrence determination process.

The boundary pixel removal process S105 shown in FIG. 4 will first be described. FIG. 7 shows a partial enlargement view of the boundary 92A between the muscle 82 and the white adipose 76. The muscle 82 comprises a plurality of muscle pixels 96 and the white adipose comprises a plurality of white adipose pixels 98. A plurality of pixels 100 having the intermediate CT numbers are present on the boundary 92A.

In the boundary pixel removal process, a filtering process is applied for each candidate pixel. In the filtering process, as shown in FIG. 8, a predetermined number (for example, 8) of pixels R1-R8 present surrounding a candidate pixel Q of interest are checked. When at least one of the pixels R1-R8 has a CT number which is higher than a first threshold value (for example, CTmax) and at least one of the pixels R1-R8 has a CT number which is lower than a predetermined second threshold value (for example, CTmin), that is, when there are both a high CT number pixel and a low CT number pixel, the candidate pixel of interest is identified as an erroneous pixel and is removed from the candidate pixels.

More specifically, in the particular boundary as described above, because the muscle and the white adipose are adjacent to each other, when a filter is set on the boundary, the filter is set over two regions and the high CT number pixel and the low CT number pixel are simultaneously captured in the filter. Thus, the erroneous pixels can be identified taking advantage of such a property of the boundary structure.

Figure 9:
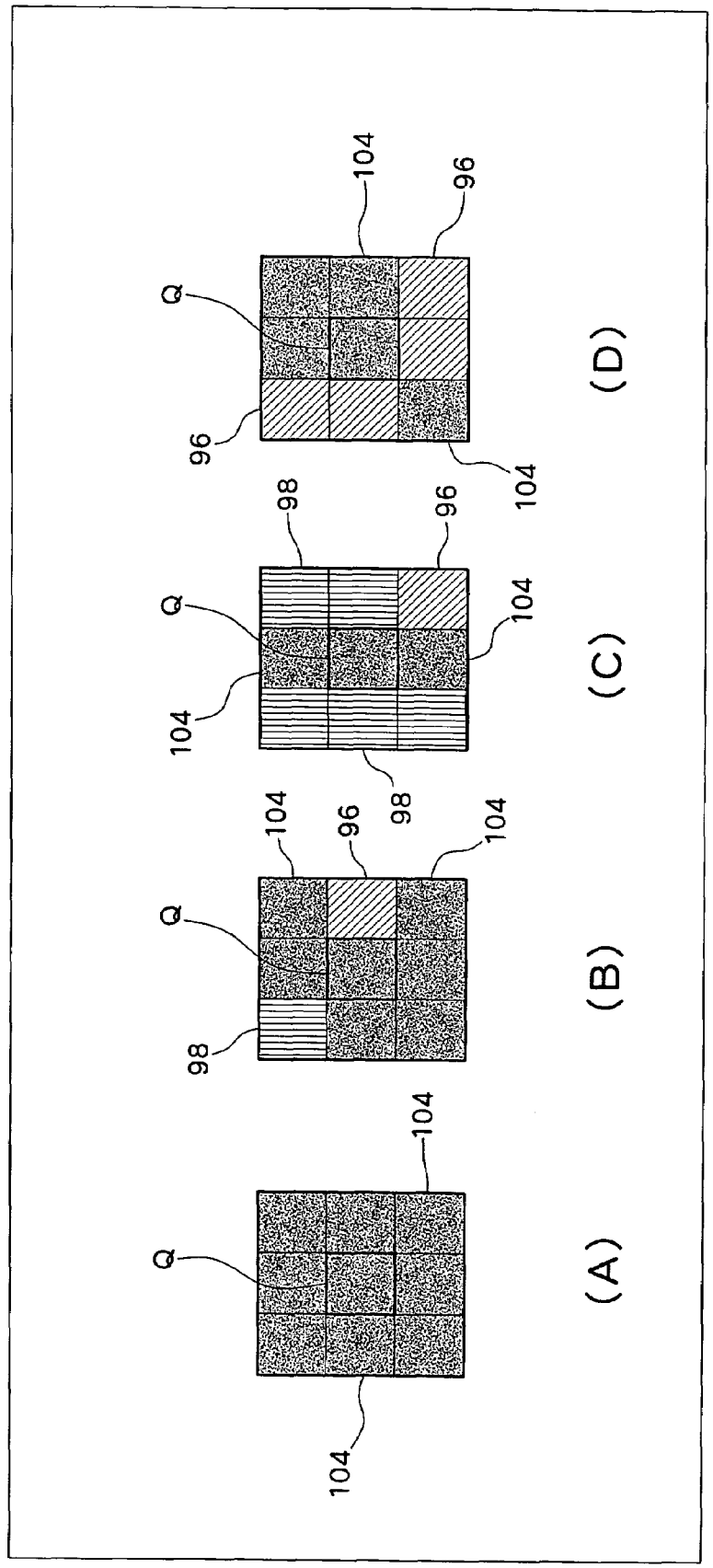
FIG. 9 is a diagram for explaining a specific example of a concurrence determination process.

FIG. 9 shows a number of examples of filtering, that is, concurrence determination processes. In the case of (A), all pixels 104 around the candidate pixel Q of interest are candidate pixels, and, thus, the candidate pixel Q of interest is not set as a candidate pixel to be removed. In the case of (B), one white adipose pixel 98 and one muscle pixel 96 are present around the candidate pixel Q of interest, and, in this case, the concurrence determination condition is satisfied and the candidate pixel Q of interest is set as a candidate pixel to be removed. In the case of (C), a number of white adipose pixels 98 and one muscle pixel 96 are present in addition to the candidate pixel 104 around the candidate pixel Q of interest, and, thus, the above-described concurrence condition is satisfied and, as a result, the candidate pixel Q of interest is set as a candidate pixel to be removed. In the case of (D), although a plurality of candidate pixels 104 and a plurality of muscle pixels 96 are present around the candidate pixel Q of interest, as there is no high CT number pixel, the candidate pixel Q of interest is maintained.

In the above-described processing examples, 8 surrounding pixels of the candidate pixel of interest are checked. The present invention, however, is not limited to such a configuration, and it is also possible to alternatively employ a configuration in which four pixels which are above, below, on the right of, and on the left of the candidate pixel of interest are checked or a configuration in which a range of pixels within a distance of two pixels from the candidate pixel of interest (that is, 15 pixels) are checked. It is also possible to use a three-dimensional filter.

Figure 10:
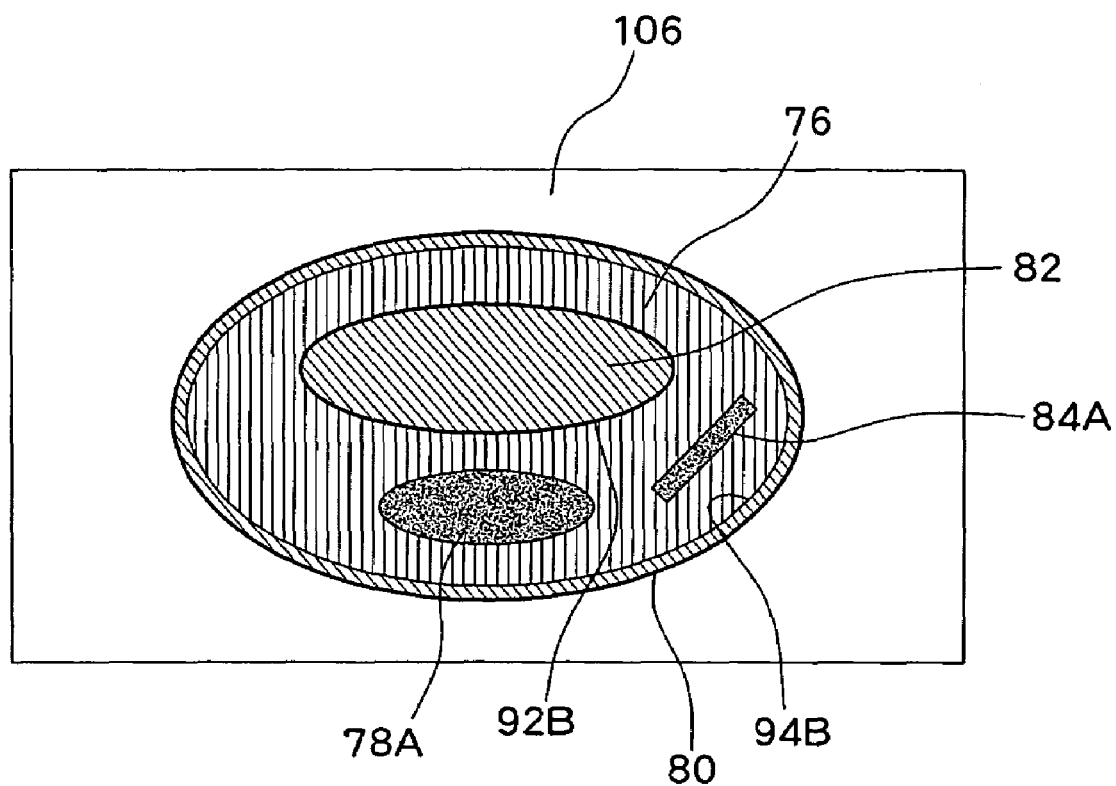
FIG. 10 is a diagram showing a result of a boundary pixel removal process.

FIG. 10 shows a result of execution of the boundary pixel removal process as described above. Specifically, as is clear from comparison of the image 106 with the image 90 shown in FIG. 6, in the image 106, a line of the candidate pixels on the boundaries 92A and 94A are removed (refer to 92B and 94B). Even when the boundary pixel removal process as described above is applied, however, as shown in FIG. 10, it may not be possible to effectively remove the thin muscle layer 84A, depending on the spatial resolution of the image. Therefore, a contraction and expansion process is executed in order to remove these candidate pixels belonging to the thin muscle layer 84A, as shown in FIG. 4.

Figure 11:
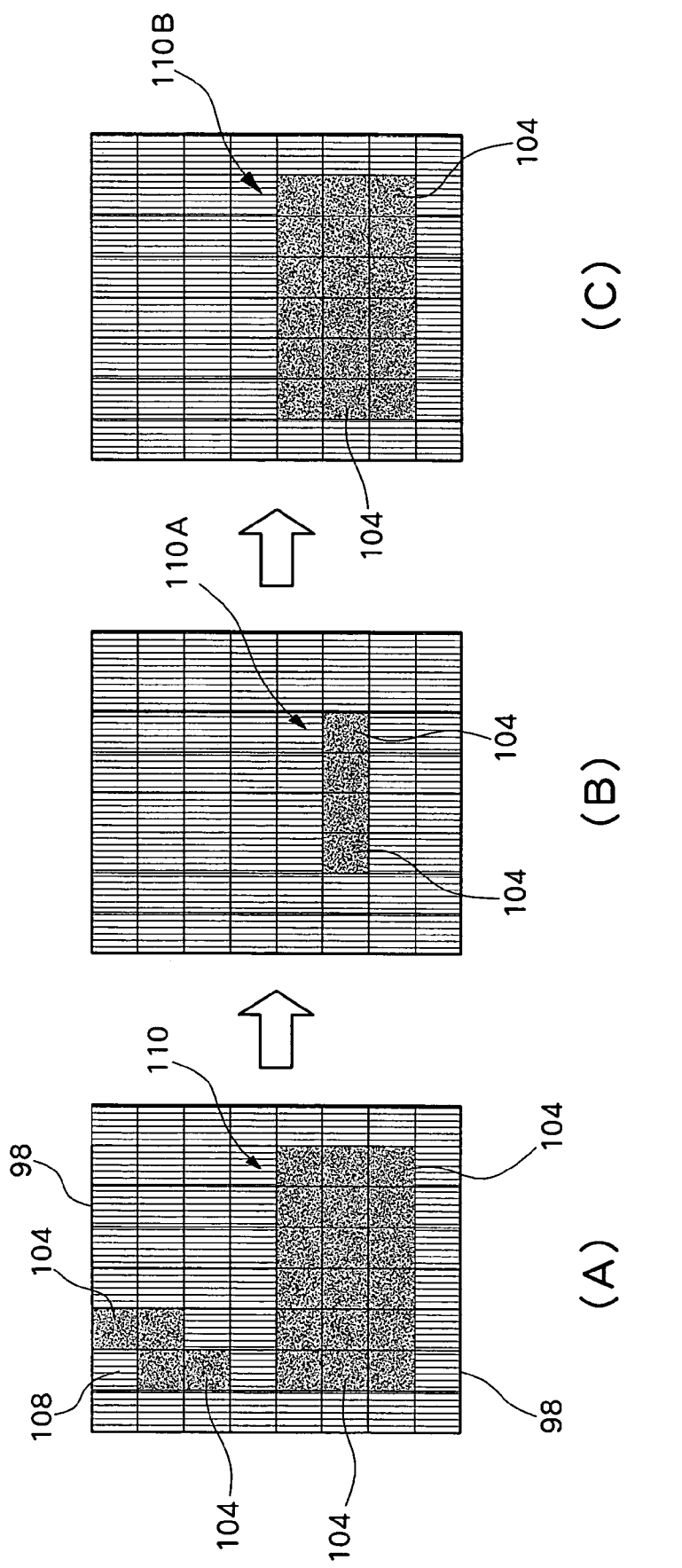
FIG. 11 is a diagram for explaining a contraction and expansion process.

FIG. 11 exemplifies a contraction and expansion process. An image (a portion of the image) before the contraction and expansion process is applied is shown in (A). A reference numeral 110 represents a brown adipose and a plurality of candidate pixels 104 are identified covering the entire brown adipose. A reference numeral 108 represents a thin muscle layer which should be filled with muscle pixels. However, because a white adipose layer is present around the thin muscle layer 108, the thin muscle layer 108 at this point is recognized as a plurality of candidate pixels 104. A reference numeral 98 represents a white adipose pixel.

After N contraction processes are applied to such an image, N expansion processes are applied. N is an integer greater than or equal to 1 and is set automatically or by a user. In the contraction process, each candidate pixel is taken as a candidate pixel of interest, 8 pixels around the pixel of interest are checked, and, when at least one white adipose pixel is present among the 8 pixels, the candidate pixel of interest is determined to be an erroneous pixel and is removed from the candidate pixels. In this case, the candidate pixel of interest is replaced with, for example, a white adipose pixel. (B) in FIG. 11 shows a result of application of one contraction process with respect to the image shown in (A). As shown in this drawing, the thin muscle layer 108 present in the image of (A) is removed and, in addition, the periphery of the brown adipose 110 is also removed. As a result, the size of the brown adipose 110 is reduced (refer to 110A).

In the expansion process, each white adipose pixel in the image after the contraction process is considered to be a white adipose pixel of interest, 8 pixels around the white adipose pixel of interest are checked, and, when a candidate pixel is present in the 8 pixels, the white adipose pixel of interest is replaced with (restored to) the candidate pixel. A result of this process is shown in (C) on FIG. 11. As is clear from comparison of this (C) with the image of (B) in FIG. 11, the brown adipose shown by the reference numeral 110B is restored to the original size. Although the exact original shape of the brown adipose generally cannot be completely restored after the contraction and expansion process, a shape close to that of the original shape can be restored.

When the thickness of the thin muscle layer to be removed is 2 pixels or less, it is sufficient to apply one contraction process and one expansion process. When the muscle layer is thick and the thickness exceeds two pixels, it is preferable to apply a plurality of contraction processes and a same number of expansion processes.

Figure 12:
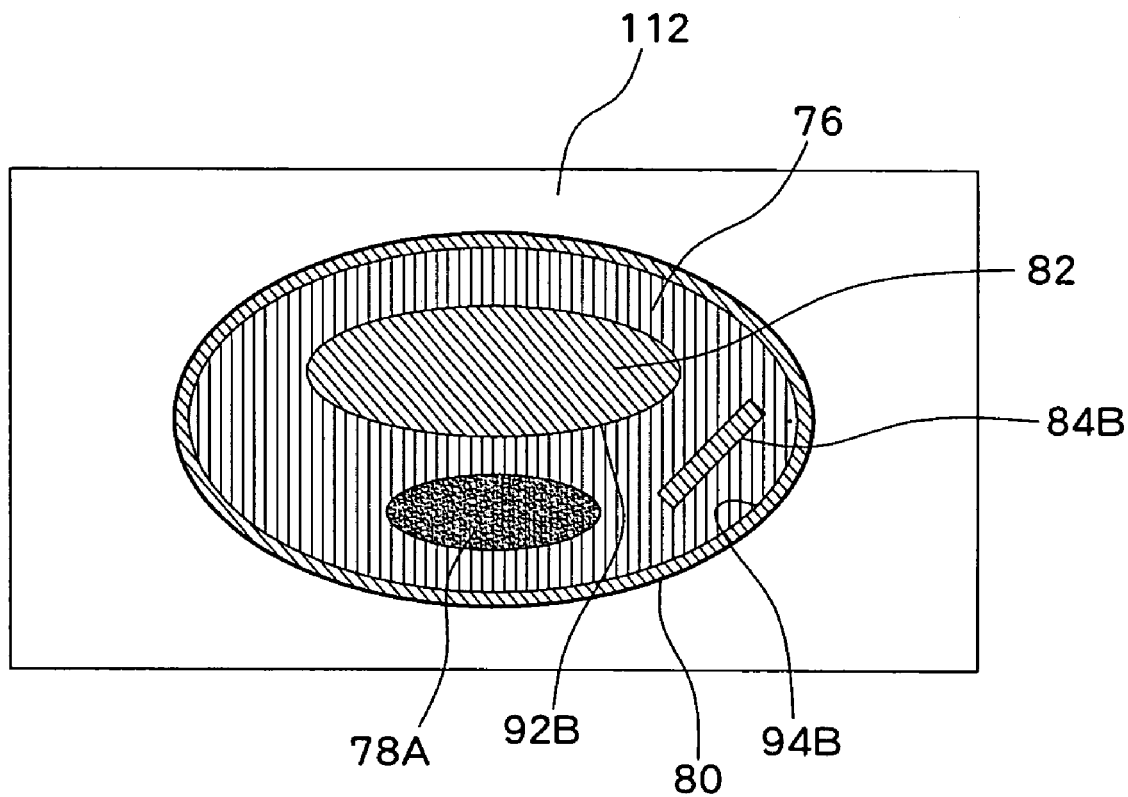
FIG. 12 is a diagram showing a result of an erroneous pixel removal process.

As a result of the contraction and expansion process, an image 112 after the brown adipose extraction process with a thin muscle layer 84B as shown in FIG. 12 can be obtained. Only the candidate pixels on the brown adipose shown by a reference numeral 78A remain. These candidate pixels are considered to be brown adipose pixels. Therefore, by counting the number of pixels forming the brown adipose pixels for each CT image, it is possible to determine the area of the brown adipose. Similarly, by applying similar processes to a plurality of CT images, it is possible to determine the volume of the brown adipose from a total area (or the total number of pixels). Furthermore, by multiplying the volume by a constant coefficient, it is possible to calculate the weight of the brown adipose.

Figure 13:
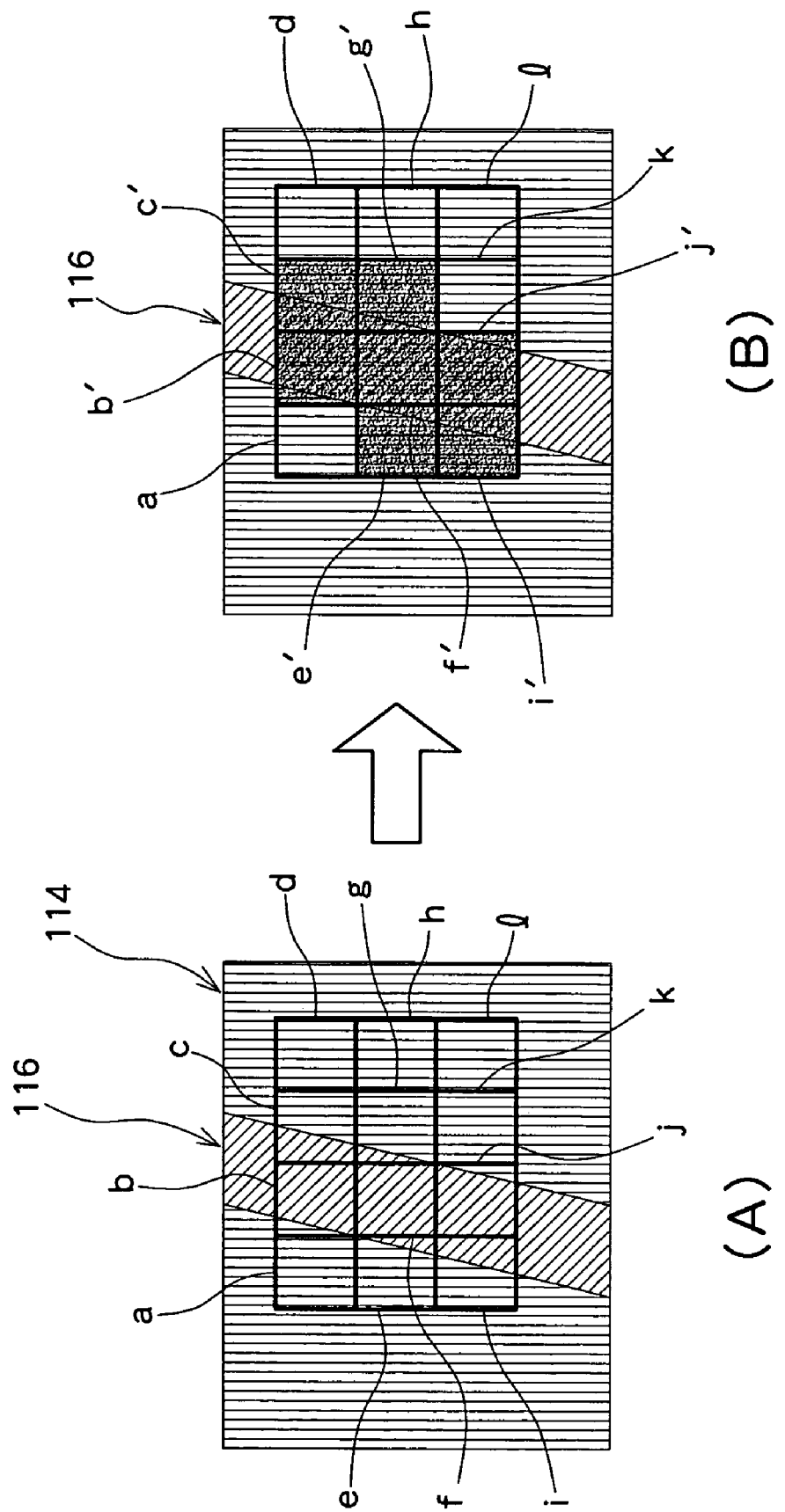
FIG. 13 is a diagram showing a result of an extraction process of candidate pixels in a case of a low spatial resolution.
Figure 14:
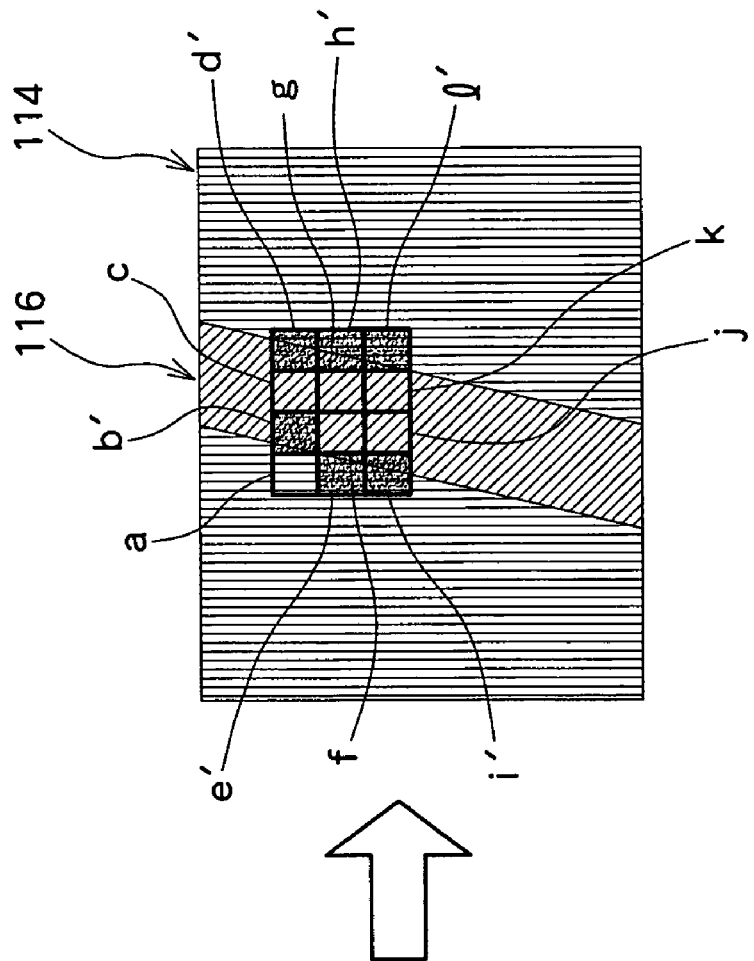
FIG. 14 is a diagram showing a result of an extraction process of candidate pixels in a case of a high spatial resolution.
Figure 14:
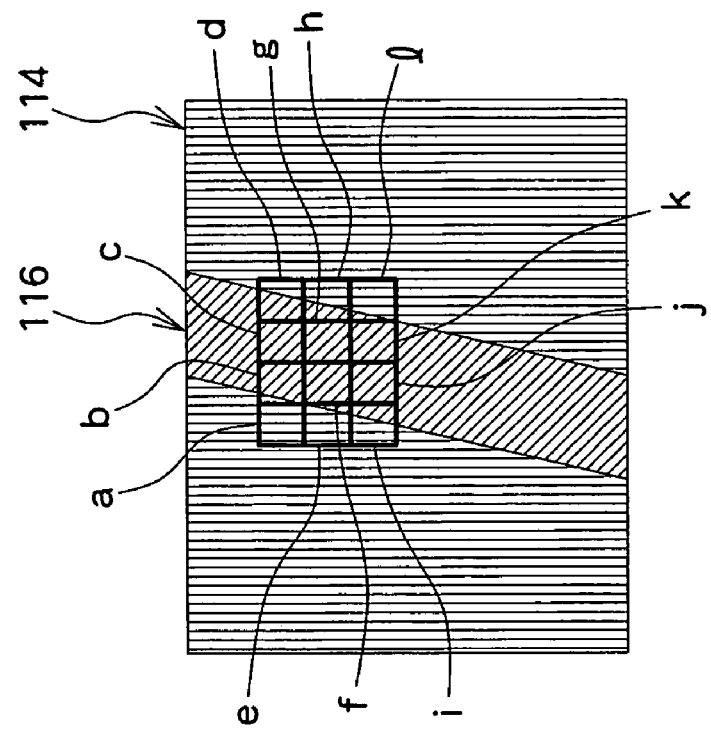

The above-described contraction and expansion process is particularly effective when the spatial resolution of the image is not sufficient, as will be described below. FIGS. 13 and 14 show presence of a thin muscle layer 116 in white adipose 114 on a CT image. In FIGS. 13 and 14, (A) shows an image before the candidate pixel extraction process is applied and (B) shows an image after the candidate pixel extraction process is applied.

As shown in FIG. 13, when the spatial resolution is low, of 12 pixels shown by a-l in (A), 7 pixels including b', c', e', f', g', i', and j' shown in (B) are recognized as candidate pixels. In other words, pixels that should be recognized as the muscle pixels are recognized as candidate pixels because of the surrounding white adipose. Therefore, when the spatial resolution is low, it is difficult to remove these erroneous pixels solely by the boundary pixel removal process as shown in FIG. 9, and, thus, it is preferable to additionally apply the above-described contraction and expansion process. When, on the other hand, the spatial resolution is high as shown in FIG. 14, of the 12 pixels of a-l in (A), 6 pixels including b', d', e', h', i', and l' shown in (B) are recognized as candidate pixels as a result of the candidate pixel extraction process. These pixels form approximately two lines (two lines of candidate pixels), and, because each line is very thin, it is possible to effectively remove a plurality of candidate pixels forming each line as erroneous pixels by applying the boundary pixel removal process as described above. Therefore, when the spatial resolution is high, it may not be necessary to apply the contraction and expansion process (refer to S111 of FIG. 4).

Processes of S106 and S107 shown in FIG. 4 will now be described referring to FIGS. 15 and 16. S106 and S107 are applied in place of S105. Alternatively, it is also possible to apply both processes in an overlapping manner. In addition, S106 and S107 are basically selectively executed. In S106, a pixel having a CT number which is greater than or equal to a predetermined third threshold value (for example, CTmax) is identified on the CT image and the candidate pixel is set as a pixel to be removed when a candidate pixel is present in a plurality of pixels present in the surroundings of the pixel. In this process, 8 surrounding pixels may be checked, or 15 surrounding pixels may be checked. Alternatively, it is also possible to consider a different number of surrounding pixels. The pixel which is set as a pixel to be removed is removed from the candidate pixels, and, in this case, it is also possible to employ a configuration in which the pixel is replaced with a tissue pixel other than the brown tissue as necessary.

Figure 15:
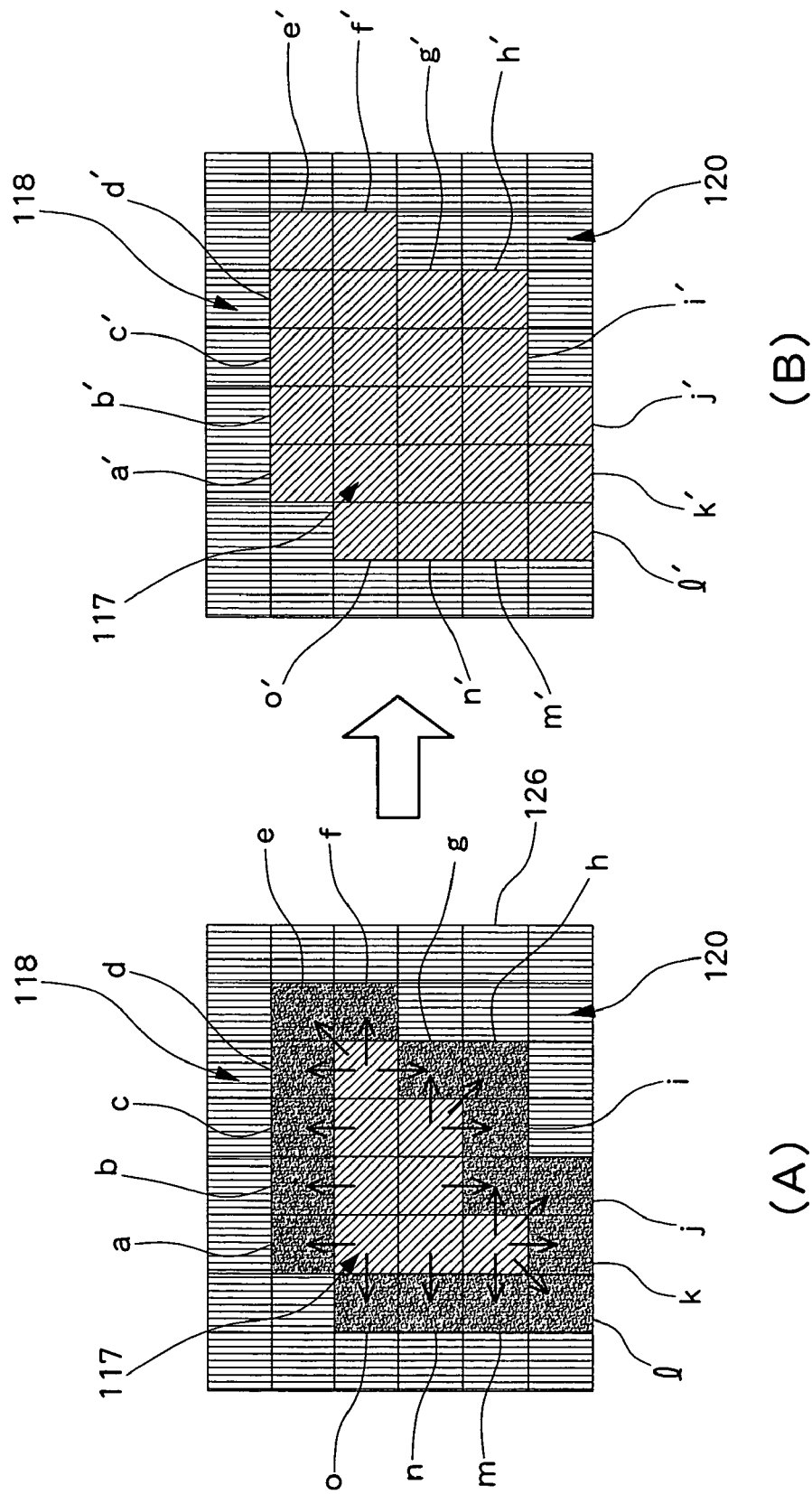
FIG. 15 is a diagram for explaining a process to remove pixels around a high CT number pixel.
Figure 16:
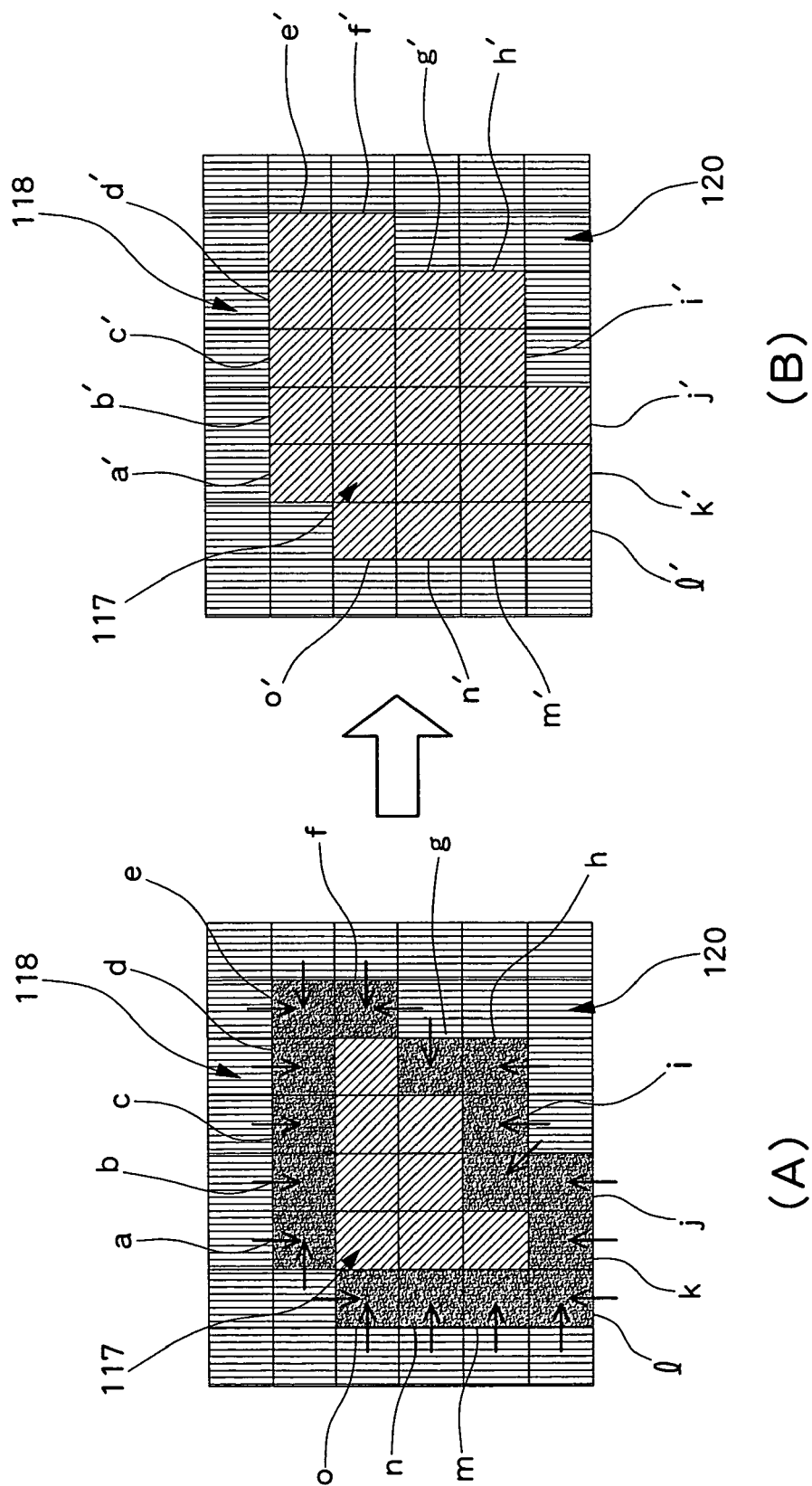
FIG. 16 is a diagram for explaining a process to remove pixels around a low CT number pixel.

FIG. 15 illustrates specific examples of the process of S106. As shown in (A), a plurality of candidate pixels a-o are present on a boundary 118 between muscle 117 having a high CT number and white adipose 120. When the above-described boundary pixel removal process is applied to such an image, a result as shown in (B) can be obtained. In other words, all candidate pixels a-o are removed from the candidate pixels and are replaced with a pixel other than the candidate pixel (in this case, muscle pixel). These pixels are shown as a'-o' in (B).

In the above-described process, a non-brown adipose tissue having a high CT number which clearly differs from that of the brown adipose are considered and the candidate pixels around such a tissue are removed. It is alternatively also possible to consider an opposite type of tissue. In other words, it is possible to consider a tissue having a low CT number which clearly differs from that of the brown adipose (for example, white adipose) and remove the candidate pixels around the tissue. This process corresponds to the process of S107 for removing pixels surrounding the low CT number pixel as shown in FIG. 4.

S107 will now be described in detail referring to FIG. 16. (A) in FIG. 16 shows an image identical to the image shown in (A) in FIG. 15. When the above-described process S107 is applied to this image, each pixel displaying white adipose (white adipose pixel) is identified, and, for each white adipose pixel, a predetermined number of pixels present around the white adipose pixels are checked, and, when the surrounding pixels include a candidate pixel, the candidate pixel is set as a pixel to be removed. A result of the process is shown in (B). Similar to the above, the candidate pixels a-o are replaced by pixels other than the candidate pixel. When such a process is to be applied, the white adipose pixel can be identified by identifying a pixel having a CT number which is less than or equal to a predetermined fourth threshold value (for example, CTmin) as the pixel of interest. In such a case, it is possible to arbitrarily set the consideration range around the pixel of interest according to circumstances, similar to the above-described process.

As a result of the execution of the process S107, a result similar to the above-described contraction process can also be obtained at the same time, and, thus, the process of step S108 shown in FIG. 4 can be omitted. With the processes of S106 and S107 also, it is possible to remove the candidate pixels on the boundary or the like, but a certain width of surrounding pixels of the brown adipose may be removed also. Therefore, if such a problem becomes significant, it is preferable to execute the processes of S105 and S108 as described above.

In either case, according to the brown adipose extraction process as described above, the brown adipose can be objectively extracted, and, thus, it is possible to prevent variation in analysis results among individuals when a region of the brown adipose is manually extracted, and to improve reliability of the measurement results. In addition, because the above-described processes are based on simple image calculation, a quick process can be expected. In other words, the brown adipose image can be quickly formed.

According to the above-described brown adipose extraction process, only the brown adipose pixels are extracted as described above, and, thus, it is possible to determine an area of the brown adipose on the processed CT image by counting a number of pixels forming the brown adipose pixels. Then, by applying a similar process to a plurality of CT images, it is possible to calculate a volume or a weight of the spatially present brown adipose as a sum of the areas.

According to the present embodiment, it is possible to measure an amount of brown adipose which has not been possible in the device of the related art. Therefore, the present invention can advantageously provide useful information for diagnosing disease and health management in the medical field. Various forms may be considered for the candidate pixel extraction process as the first extraction process and the erroneous pixel removal process as the second extraction process. In any event, by removing the erroneous pixels after extracting candidate pixels as necessary, it is possible to obtain a highly precise extraction result.

(4) Calculation Of Evaluation Value

Figure 17:
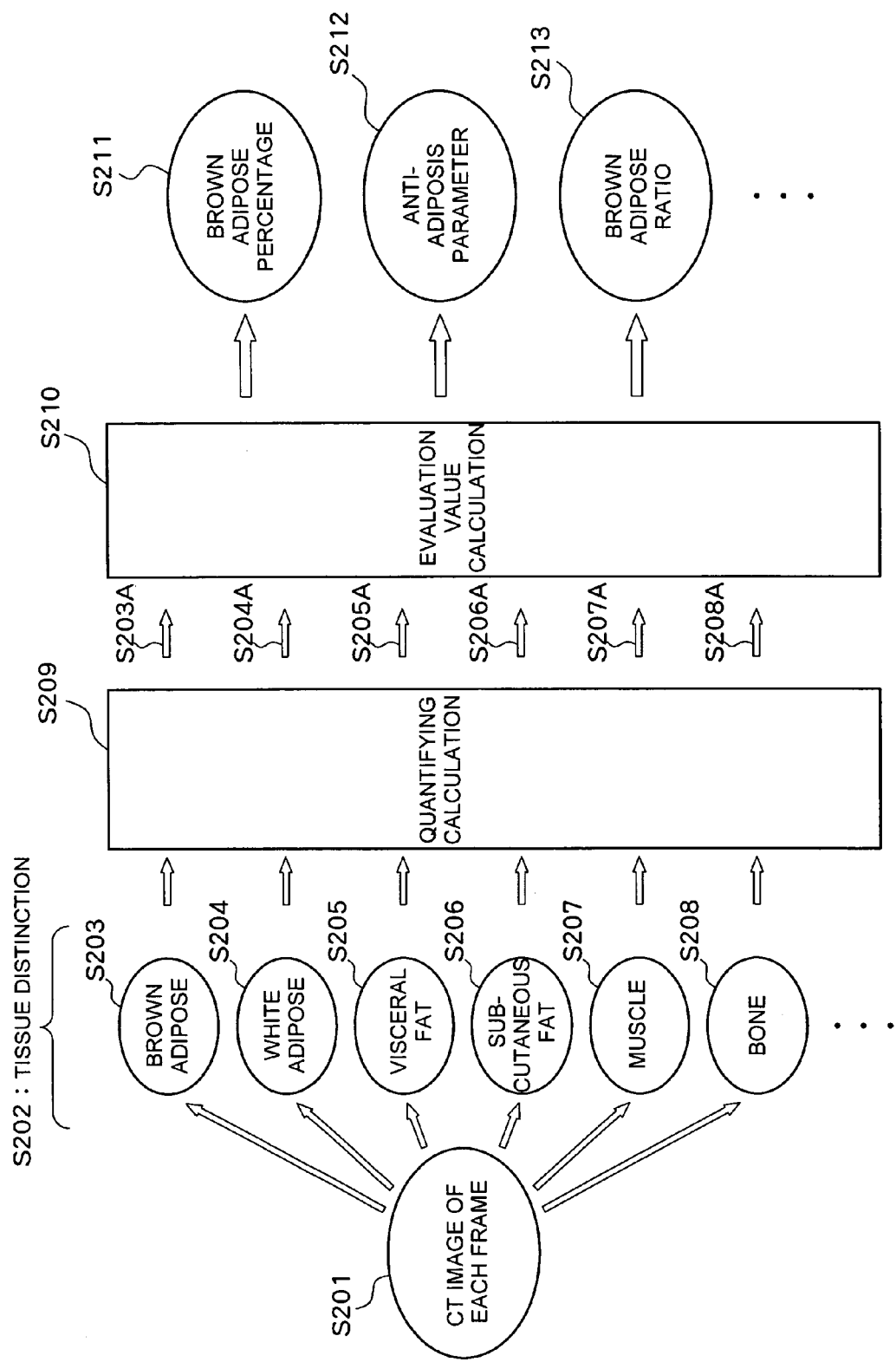
FIG. 17 is a flowchart for explaining a calculation method of an evaluation value.

A calculation of an evaluation value based on the amount of brown adipose will now be described referring to FIGS. 17-18. FIG. 17 conceptually shows a flow of the evaluation value calculation.

S201 shows a CT image of each frame. For each frame CT image, a process to be described below is applied. S202 shows a tissue distinguishing process. In other words, in the tissue distinguishing process S202, the tissues are identified on the CT image. S203 represents an extraction process of brown adipose. A representative example of this process is the process shown in FIG. 4. S204 represents a white adipose extraction process and, a representative example of this process is the process shown in FIG. 4. In other words, the white adipose can be extracted in a process similar to that for the brown adipose.

S205 indicates a visceral fat extraction process and S206 represents a subcutaneous fat extraction process. As these processing methods, for example, it is possible to employ methods as described in Japanese Patent Laid-Open Publication No. 2003-339694. S207 represents a muscle extraction process and S208 represents a bone extraction process. Known methods can be employed for these processes. In other words, it is possible to identify these tissues by a distinguishing process based on the CT number. Alternatively, it is also possible to incorporate other additional extraction processes in the tissue distinguishing process S202 as necessary.

S209 represents a quantitative calculation process. Specifically, when tissues are extracted on the image by the extraction processes S203-S208, the amount of tissue for each tissue is calculated in the quantitative calculation process of S209. The amount of tissue corresponds to a number of pixels, an area, a volume, or a weight. For example, the volume can be easily calculated for each tissue by determining the sum of the areas or numbers of pixels calculated for a plurality of frames.

S203A-S208A represent amounts of tissues as a result of the quantitative calculation of S209. The weight of each tissue can be calculated by multiplying the volume of the tissue by a predetermined conversion factor (specific gravity). For example, the specific gravity of the white adipose is 0.92 (g/cm$^3$) and the specific gravity of the muscle is 1.06 (g/cm$^3$). In this manner, when the specific gravity of the tissue is known, it is possible to convert to weight for each tissue using the specific gravity.

The amount of bone can be determined through the following calculation. In the following equation, BMC (bone mineral content) represents an amount of bone (weight of mineral in the bone) in units of grams.

$$BMC = \sum_{x=0}^{r-1} \sum_{y=0}^{s-1} \sum_{z=0}^{t-1} (BMD_{xyz} \times V) \quad (2\text{-}1)$$

$$BMD_{xyz} = aX + b \quad (2\text{-}2)$$

In the above-described equation (2-2), the parameter BMDxyz represents a bone density, in units of g/cm$^3$, of a bone pixel positioned at a coordinate of (x,y) in a zth frame. The parameter X represents a CT number (HU) for the bone pixel, the parameter a represents a slope as a bone density conversion factor, and the parameter b represents an intercept, which is an offset as a bone density conversion factor. In other words, when the CT number for the bone pixel is determined, the bone density for the pixel can be determined from the equation (2-2) described above.

In the above-described equation (2-1), the parameter V represents a volume (cm$^3$) per pixel, parameters r and s represent numbers of pixels along the X direction and Y direction forming the frame, and a parameter t represents a number of frames. Thus, using the equation (2-1), it is possible to determine the weight of the overall bone from the CT numbers of the pixels.

The parameters a and b can be determined in advance by applying a cross sectional imaging with respect to a plurality of phantoms. The plurality of phantoms have bone densities that are known and differ from each other.

Figure 18:
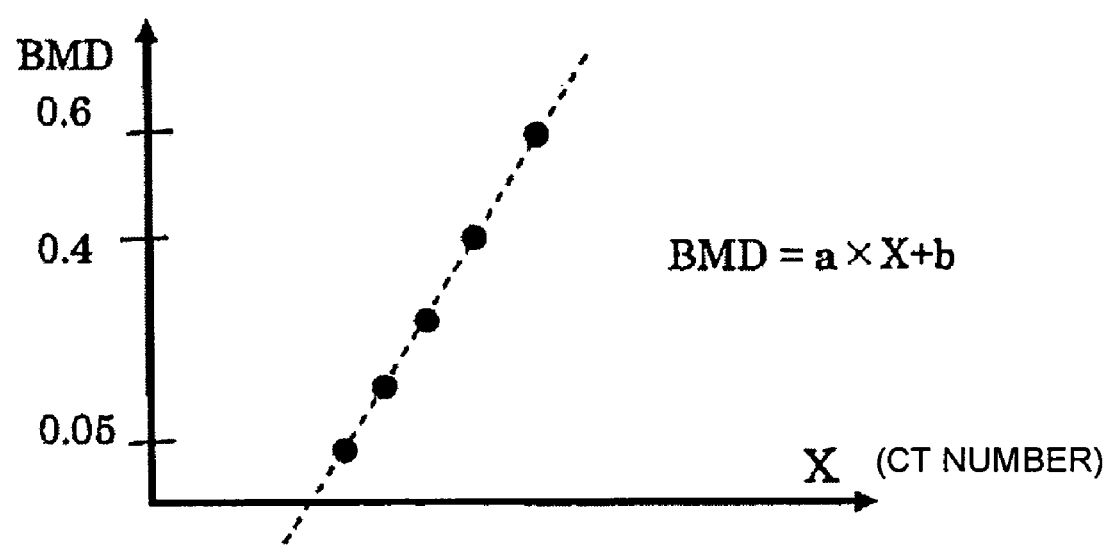
FIG. 18 is a diagram for explaining determination of a coefficient in a bone density calculation formula.

FIG. 18 shows the results of a phantom experiment. The horizontal axis represents the CT number, that is, X and the vertical axis represent BMD (bone mineral density). By plotting the measurement values for the phantoms on the coordinate system shown in FIG. 18, it is possible to find a straight line connecting the measurement points and easily determine the parameters a and b in the above-described equation.

Returning to FIG. 17, in the evaluation value calculation of S210, an evaluation value is determined by executing a calculation to be described below based on the amounts of tissues for the tissues determined as described above.

In the present embodiment, "brown adipose percentage" in S211, "anti-adiposis parameter" in S212, and "brown adipose ratio" in S213 are calculated as the evaluation values. These evaluation values will now be described in detail.

The brown adipose percentage will first be described. When the sample is large, in general, the amount of brown adipose is also large. Therefore, direct comparison of the amount of the brown adipose among different samples of different sizes would not lead to an objective evaluation and, therefore, it is desirable to apply a correction based on the physical constitution. An evaluation value determined from this point of view is the brown adipose percentage. The brown adipose percentage is determined, for example, through the following equation (3):

$$\text{Brown adipose percentage} = \text{amount of brown adipose}/\text{weight}*100(\%) \quad (3)$$

The weight in the above-described equation can be determined from a total of the amount of bone, the amount of brown adipose, the amount of white adipose, and the amount of muscle. The amount of tissue may be weight of the tissue as described above, or a value that corresponds to the volume or the area. The weight can also be directly measured using a scale or an electronic balance. In either case, by standardizing the amount of brown adipose using some index representing the physical constitution, it is possible to resolve the problem associated with the dependency on the physical constitution. Alternatively, it is also possible to define the brown adipose percentage using an equation different from the above-described equation.

Next, the anti-adiposis parameter will be described. From the viewpoint of resisting adiposis, the white adipose is simply fat and it is desirable that the amount of the white adipose be small. The amount of muscle, on the other hand, is proportional to the amount of basal metabolism, and, thus, it can be considered that higher the amount of muscle is, the lower the probability of obesity. The amount of brown adipose can be considered as being proportional to the amount of burning of the white adipose, and, thus, is preferably high. The anti-adiposis parameter is determined by incorporating these relationships in one equation. As the value of the anti-adiposis parameter is increased, the possibility that the sample becomes obese or the possibility that the sample is obese is reduced. The anti-adiposis parameter is defined by, for example, the following equation:

$$\text{Anti-adiposis parameter} = \text{amount of brown adipose}*\text{amount of muscle}/\text{amount of white adipose} \quad (4)$$

From the viewpoint of obesity, the increase in visceral fat is thought to be particularly problematic. Therefore, it is also possible to define the anti-adiposis parameter by changing the above-described equation into the following form:

$$\text{Anti-adiposis parameter} = \text{amount of brown adipose}*\text{amount of muscle}/\text{amount of visceral fat} \quad (5)$$

Next, the brown adipose ratio in adipose will be described. As described above, adipose can be classified into the white adipose and brown adipose and a ratio of the white adipose and the brown adipose can be used as an evaluation value. In other words, a ratio defined by the following equation (6) can be used as the evaluation value:

$$\text{Ratio of brown adipose in adipose} = \text{amount of brown adipose}/(\text{amount of white adipose}+\text{amount of brown adipose})*100(\%) \quad (6)$$

In the above-description, a number of evaluation values have been exemplified. In any of these evaluation values, it is possible to provide information useful for clinical purposes by determining an evaluation value based on the amount of brown adipose and correlating amounts of one or a plurality of tissues to the amount of brown adipose when it is not possible to objectively evaluate the constitutional disposition or health state based solely on the amount of brown adipose. For example, it is also possible to calculate a parameter of the amount of brown adipose versus the amount of visceral fat as the evaluation value. Moreover, it is also possible to calculate the above-described plurality of evaluation values in parallel and simultaneously display the evaluation values as numbers.

As described, according to the method, it is possible to calculate an evaluation value related to the percentage of the brown adipose based on the amount of brown adipose. Even when the sample cannot be accurately evaluated solely by the amount of brown adipose, it is possible to objectively or comprehensively evaluate a sample by determining an evaluation value in consideration of or reflecting other information, in addition to the base which is the amount of brown adipose.

(5) Various Variations

In the above-described example of the preferred embodiment, an X-ray CT device for small animal has been described. The present invention, however, is not limited to such an application and the present invention can alternatively be applied to an X-ray CT device for a human body. In other word, the brown adipose in a human body can be measured and an evaluation value based on the amount of brown adipose can be calculated through a method similar to the above-described method.

In the example used to illustrate the above-described embodiment, a fan beam is used. It is also possible to alternatively use a pencil beam or a cone beam. It is also possible to maintain the container in a vertically standing state, form the beam in the horizontal direction, and execute the CT measurement. In this case, one of the container and the beam is rotationally scanned. In the above-described example, the sample is moved and scanned, but the present invention is not limited to such a configuration and the measurement unit, that is, the beam, may be moved and scanned. The moving scan range can be set covering the whole body of the sample or covering only a specific site of the sample.

In the above-described example, two stages of processes including the first extraction process and the second extraction process are applied to a CT image. When the brown adipose can be distinguished with a high precision by the first extraction process, the second extraction process may be omitted. In order to further improve the distinction precision of the brown adipose, it is also possible to apply various image processes after the two stages of processes or before the first extraction process.

The brown adipose image is preferably displayed overlapping a background image showing the overall tissue. In this case, it is possible to form the background image as a black-and-white brightness image and form the brown adipose image as a colored image which is colored in a predetermined manner. Alternatively, when the CT image is to be displayed in color, it is possible to assign a predetermined color to each tissue, color the tissues, and display the tissues in color so that the individual tissue can be clearly distinguished on the CT image by color.

What is claimed is:

1. An X-ray computerized tomography device comprising:
an X-ray generator which irradiates a sample with an X-ray beam;

an X-ray detector which detects an X-ray beam transmitting through the sample;
a rotation mechanism which rotates the X-ray beam relatively with respect to the sample;
an image formation unit which reconstructs a CT image based on an output signal of the X-ray detector; and
an image processor which applies an image process to the CT image to distinguish brown adipose in the sample from other tissues; and
the image processor comprising:
a first extraction unit which extracts candidate pixels, from among a group of pixels reconstructing the CT image, based on a CT number of each pixel; and
a second extraction unit which applies an erroneous pixel removal process to the candidate pixels to extract brown adipose pixels.

2. An X-ray computerized tomography device according to claim 1, wherein
the first extraction unit determines whether or not a CT number of each pixel of the group of pixels is within a predetermined range and identifies a pixel having the CT number within the predetermined range as the candidate pixel.

3. An X-ray computerized tomography device according to claim 2, wherein
an upper limit of the predetermined range is determined, at a CT number between a standard CT number of muscle and CT number of brown adipose, and
a lower limit of the predetermined range is determined at a CT number between a standard CT number of white adipose and the standard CT number of the brown adipose.

4. An X-ray computerized tomography device according to claim 1, wherein
the erroneous pixel removal process in the second extraction unit comprises a first process, and
in the first process, a candidate pixel of interest is determined as an erroneous pixel and is removed when a pixel having a CT number which is higher than a first threshold value and a pixel having a CT number which is lower than a second threshold value are present around the candidate pixel of interest.

5. An X-ray computerized tomography device according to claim 1, wherein
the erroneous pixel removal process in the second extraction unit comprises a process, and
in the process, a non-brown adipose pixel satisfying a predetermined condition is identified in the CT image and, when a candidate pixel which is adjacent to the non-brown adipose pixel is present, the adjacent candidate pixel is determined as an erroneous pixel and is removed.

6. An X-ray computerized tomography device according to claim 5, wherein
the predetermined condition includes a condition to determine a pixel having a CT number which is higher than a threshold value as the non-brown adipose pixel.

7. An X-ray computerized tomography device according to claim 5, wherein
the predetermined condition includes a condition to determine a pixel having a CT number which is lower than a threshold value as the non-brown adipose pixel.

8. An X-ray computerized tomography device according to claim 1, wherein
the erroneous pixel removal process in the second extraction unit comprises a process, and
in the process, a contraction process is applied to the candidate pixels and an expansion process is applied to the candidate pixels to which the contraction process is applied.

9. An X-ray computerized tomography device according to claim 1, further comprising:
a voltage switching unit which switches a drive voltage of the X-ray generator, wherein
in a normal measurement mode, a high voltage is selected as the drive voltage of the X-ray generator, and
in a brown adipose measurement mode, a low voltage is selected as the drive voltage of the X-ray generator.

10. An X-ray computerized tomography device according to claim 9, wherein
the low voltage is a voltage within a range of 30 kV-70 kV.

11. An X-ray computerized tomography device according to claim 1, further comprising:
a rotation speed switching unit which switches a rotational speed of the X-ray beam, wherein
in a normal measurement mode, a high speed is selected as the rotational speed of the X-ray beam, and
in a brown adipose measurement mode, a low speed is selected as the rotational speed of the X-ray beam.

12. An X-ray computerized tomography device according to claim 1, wherein
the sample is an animal other than a human being.

13. An X-ray computerized tomography device according to claim 1, wherein
the sample is a human body.

14. An X-ray computerized tomography device comprising:
an X-ray generator which irradiates a sample with an X-ray beam;
an X-ray detector which detects an X-ray beam transmitting through the sample;
a rotation mechanism which rotates the X-ray beam relatively with respect to the sample;
an image formation unit which reconstructs a CT image based on an output signal of the X-ray detector; and
an image processor which applies an image process to the CT image to distinguish brown adipose in the sample from other tissues; and
a calculation unit which calculates an amount of brown adipose based on the identified brown adipose and calculates an evaluation value related to a ratio of the brown adipose present in the sample based on the amount of brown adipose and on an amount of another tissue.

15. An X-ray computerized tomography device according to claim 14, further comprising:
a scanning mechanism which relatively moves the sample with respect to the X-ray beam, wherein
the image processor applies a brown adipose identification process to a plurality of CT images corresponding to a plurality of movement positions on the sample, and
the calculation unit calculates a volume or a weight of the brown adipose as the amount of brown adipose based on a result of the brown adipose identification process with respect to the plurality of CT images.

16. An X-ray computerized tomography device according to claim 14, wherein
the image processor identifies a plurality of tissues including brown adipose and another tissue in the sample based on the CT image, and
the calculation unit calculates amounts of a plurality of tissues including an amount of the brown adipose and an amount of another tissue based on a result of the image process by the image processor and calculates the evaluation value based on the amounts of the plurality of tissues.

17. An X-ray computerized tomography device according to claim 16, wherein
the evaluation value is determined through a calculation of the amount of brown adipose divided by the sum of the amounts of the plurality of tissues.

18. An X-ray computerized tomography device according to claim 16, wherein
the amounts of the plurality of tissues include an amount of white adipose in addition to the amount of brown adipose, and
the evaluation value is determined through a calculation of the amount of brown adipose divided by the sum of the amount of brown adipose and the amount of white adipose.

19. An X-ray computerized tomography device according to claim 16, wherein
the amounts of the plurality of tissues include an amount of muscle and an amount of white adipose in addition to the amount of brown adipose, and
the evaluation value is determined through a calculation of the amount of brown adipose multiplied by the amount of muscle divided by the amount of white adipose.

20. An X-ray computerized tomography device according to claim 16, wherein
the amounts of the plurality of tissues include an amount of muscle and an amount of visceral fat in addition to the amount of brown adipose, and
the evaluation value is determined through a calculation of the amount of brown adipose multiplied by the amount of muscle divided by the amount of visceral fat.

21. An X-ray computerized tomography device comprising:
an X-ray generator which irradiates a sample with an X-ray beam;
an X-ray detector which detects an X-ray beam transmitting through the sample;
a rotation mechanism which rotates the X-ray beam relatively with respect to the sample;
an image formation unit which reconstructs a CT image based on an output signal of the X-ray detector; and
an image processor which applies an image process to the CT image to distinguish brown adipose in the sample from other tissues; and
a calculation unit which calculates an amount of brown adipose based on the identified brown adipose and calculates an evaluation value to be determined through a calculation of the amount of brown adipose divided by the weight of the sample.

22. An image processing method in which a CT image obtained through an X-ray computerized tomography measurement with respect to a sample is processed, the method comprising:
a first extraction step in which candidate pixels determined as possibly displaying a brown adipose are extracted from a group of pixels reconstructing the CT image based on a CT number of each pixel; and
a second extraction step in which an erroneous pixel removal process is applied to the candidate pixels to extract brown adipose pixels.

23. An image processing method according to claim 22, wherein
in the first extraction process, a determination is made for each pixel of the group of pixels as to whether or not a CT number of the pixel is within a predetermined range and a pixel having the CT number within the predetermined range is identified as the candidate pixel;
an upper limit of the predetermined range is set at a level for distinguishing between muscle and the brown adipose, and
a lower limit of the predetermined range is set at a level for distinguishing between white adipose and the brown adipose.

24. An image processing method according to claim 22, wherein
the erroneous pixel removal process in the second extraction step comprises a first process, and
in the first process, a candidate pixel of interest is determined as an erroneous pixel and is removed when a pixel having a CT number which is higher than a first threshold value and a pixel having a CT number which is lower than a second threshold value are present around the candidate pixel of interest.

25. An image processing method according to claim 22, wherein
the erroneous pixel removal process in the second extraction step comprises a process, and
in the process, a non-brown adipose pixel which satisfies a predetermined condition is identified on the CT image, and, when a candidate pixel which is adjacent to the non-brown adipose pixel is present, the adjacent candidate pixel is determined as an erroneous pixel and is removed.

26. An image processing method according to claim 22, wherein
the erroneous pixel removal process in the second extraction step comprises a process, and
in the process, a contraction process is applied to the candidate pixels and an expansion process is applied to the candidate pixels to which the contraction process is applied.

27. An image processing method according to claim 22, further comprising
a quantifying step in which the brown adipose is quantified based on the number of brown adipose pixels extracted.

28. An image processing method according to claim 27, wherein
at least one of an area, a volume, and a weight is calculated for the brown adipose by the quantification.

29. An image processing method according to claim 22, further comprising:
a step in which an amount of brown adipose is calculated based on a number of pixels of the extracted brown adipose pixels, and
a step in which an evaluation value related to a percentage of the brown adipose present in the sample is calculated based on the amount of brown adipose.

30. An image processing method according to claim 29, wherein
the evaluation value is defined as a ratio between an amount of a predetermined tissue and the amount of the brown adipose.

* * * * *